(12) United States Patent
Gupta et al.

(10) Patent No.: US 8,954,152 B2
(45) Date of Patent: *Feb. 10, 2015

(54) METHOD AND APPARATUS FOR EVENT-TRIGGERED REINFORCEMENT OF A FAVORABLE BRAIN STATE

(71) Applicant: Medtronic, Inc., Minneapolis, MN (US)

(72) Inventors: Rahul Gupta, St. Louis Park, MN (US); Gabriela C. Molnar, Fridley, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/892,401

(22) Filed: May 13, 2013

(65) Prior Publication Data

US 2013/0245714 A1 Sep. 19, 2013

Related U.S. Application Data

(63) Continuation of application No. 13/090,672, filed on Apr. 20, 2011, now Pat. No. 8,473,063.

(60) Provisional application No. 61/385,412, filed on Sep. 22, 2010.

(51) Int. Cl.
*A61N 1/32* (2006.01)
*A61N 1/36* (2006.01)
(Continued)

(52) U.S. Cl.
CPC ............ *A61N 1/3606* (2013.01); *A61N 1/0529* (2013.01); *A61N 1/36025* (2013.01);
(Continued)

(58) Field of Classification Search
CPC ............ A61N 1/0529; A61N 1/36025; A61N 1/3606; A61N 2001/36039
USPC .................................................. 607/45, 48, 62
See application file for complete search history.

(56) References Cited

U.S. PATENT DOCUMENTS 6,066,163 A * 5/2000 John ............................... 607/45
6,463,328 B1 10/2002 John
(Continued)

FOREIGN PATENT DOCUMENTS

CA 2607374 A1 * 4/2009
WO 2010085518 A1 7/2010

OTHER PUBLICATIONS

Engineer et al., "Reversing Pathological Neural Activity Using Targeted Plasticity," Nature, vol. 470, pp. 101-106, Feb. 3, 2011.
(Continued)

*Primary Examiner* — Christopher D Koharski
*Assistant Examiner* — Michael Carey
(74) *Attorney, Agent, or Firm* — Shumaker & Sieffert, P.A.

(57) ABSTRACT

Methods and apparatuses are disclosed for potentiating a favorable brain state that is associated with relief in symptoms of a brain condition. Techniques include monitoring one or more brain signals and detecting an episode of a favorable brain state based on the one or more brain signals, the favorable brain state associated with a decrease in one or more symptoms of a brain condition of the patient. Then, in response to the detection of the favorable brain state episode, electrical stimulation that potentiates the favorable brain state is delivered to the brain of the patient, the electrical stimulation delivered within a window of time opened for detection of each favorable brain state episode.

39 Claims, 5 Drawing Sheets

(51) Int. Cl.
*A61N 1/05* (2006.01)
*A61B 5/00* (2006.01)

(52) U.S. Cl.
CPC ........ *A61N1/36139* (2013.01); *A61N 1/36167* (2013.01); *A61N 2001/36039* (2013.01); *A61B 5/4064* (2013.01); *A61B 5/4082* (2013.01); *A61B 5/4094* (2013.01); *A61B 5/6868* (2013.01); *A61N 1/36064* (2013.01); *A61N 1/36067* (2013.01); *A61N 1/36071* (2013.01); *A61N 1/36082* (2013.01)
USPC .................................. 607/45; 607/48; 607/62

(56) References Cited

U.S. PATENT DOCUMENTS

| | | | |
|---|---|---|---|
| 7,499,752 | B2 | 3/2009 | Maschino et al. |
| 7,555,344 | B2 | 6/2009 | Maschino et al. |
| 7,787,946 | B2 | 8/2010 | Stahlmann et al. |
| 8,473,063 | B2 * | 6/2013 | Gupta et al. .................... 607/46 |
| 2007/0208212 | A1 | 9/2007 | DiLorenzo |
| 2008/0045775 | A1 | 2/2008 | Lozano |
| 2009/0099627 | A1 | 4/2009 | Molnar et al. |
| 2009/0264954 | A1 * | 10/2009 | Rise et al. ....................... 607/45 |

OTHER PUBLICATIONS

Jackson et al., "Long-Term Motor Cortex Plasticity Induced by an Electronic Neural Implant," Nature, vol. 444, pp. 56-60, Nov. 2, 2006.
International Search Report from PCT Application No. PCT/US2011/052346, dated Feb. 20, 2012, 4 pp.
Written Opinion of the International Searching Authority from PCT Application No. PCT/US2011/052346, dated Feb. 20, 2012, 8 pp.
Prosecution history from U.S. Appl. No. 13/090,672, dated Sep. 17, 2012, through May 9, 2013, 53 pp.

* cited by examiner

METHOD AND APPARATUS FOR EVENT-TRIGGERED REINFORCEMENT OF A FAVORABLE BRAIN STATE

This application is a continuation, and claims the benefit, of U.S. patent application Ser. No. 13/090,672, filed Apr. 20, 2011, which issued as U.S. Pat. No. 8,473,063 on Jun. 25, 2013, and which claims the benefit of U.S. Provisional Patent Application Ser. No. 61/385,412, filed Sep. 22, 2010, the entire contents of both of which are incorporated herein by reference.

TECHNICAL FIELD

The disclosure relates to medical systems, and, more particularly, medical systems that deliver electrical stimulation to potentiate a favorable brain state.

BACKGROUND

Implantable medical devices, such as electrical stimulation devices, may be used in different therapeutic applications, such as for deep brain stimulation, spinal cord stimulation, pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain. In some therapy systems, an implantable electrical stimulator delivers electrical therapy to a target tissue site within a patient with the aid of one or more electrodes, which may be deployed by medical leads.

SUMMARY

In general, the disclosure relates to methods, systems, and devices for delivering electrical stimulation to potentiate a favorable brain state.

Various embodiments concern a method of potentiating a favorable brain state of a patient, comprising: monitoring one or more brain signals; detecting an episode of a favorable brain state based on the one or more brain signals, the favorable brain state associated with a decrease in one or more symptoms of a brain condition of the patient; and delivering electrical stimulation that potentiates the favorable brain state to the brain of the patient in response to the detection of the favorable brain state episode, the electrical stimulation delivered within a window of time that extends no greater than 250 milliseconds from occurrence of the favorable brain state episode, wherein monitoring, detecting, and delivering are each performed at least in part by control circuitry of a medical device. Such methods may further include assessing the one or more symptoms of the brain condition of the patient; analyzing brain information indicative of one or more brain states; and identifying the favorable brain state from the one or more brain states, the favorable brain state identified based on a decrease in the one or more symptoms of the brain condition.

In various method embodiments, detecting the favorable brain state episode comprises recognizing one or more patterns in the one or more brain signals that correspond to one or more stored biomarkers of the favorable brain state, the favorable brain state episode is detected based on a power level of a frequency band of the one or more signals crossing a threshold, and/or the favorable brain state episode comprises the brain transitioning from one brain state to a different brain state. Various method embodiments include titrating one or more delivery parameters of the electrical stimulation to increase the potentiation effect of the electrical stimulation on the favorable brain state, titrating one or more delivery parameters of the electrical stimulation based on increasing one or both of frequency and duration of occurrence of the favorable brain state, and/or titrating one or more delivery parameters of the electrical stimulation based on increasing an amplitude of the one or more signals indicative of the favorable brain state.

Various method embodiments include, identifying one or more brain signal biomarkers of the patient as indicative of the favorable brain state; and storing the one or more brain signal biomarkers in memory, wherein detecting the favorable brain state episode comprises recognizing presence of the one or more biomarkers in the one or more brain signals. In various method embodiments, the electrical stimulation comprises only one or two pulses delivered within the window of time which is opened for each detection of occurrence of the favorable brain episode, and/or the electrical stimulation is timed to coincide with a particular phase of the one or more brain signals that indicate the favorable brain state episode. In various method embodiments, the favorable brain state event comprises detecting a plurality of favorable brain state events; and delivering the electrical stimulation comprises delivering one or more pulses to the brain within the window of time respectively for each of the plurality of favorable brain state episodes detected. In various method embodiments, the window of time spans from the beginning of occurrence of the favorable brain state episode and extends no greater than 100 milliseconds from the end of occurrence of the favorable brain state episode. In various method embodiments, the one or more brain signals comprise one or more local field potential signals sensed from implanted electrodes.

Various embodiments concern a system comprising: one or more sensors configured to receive one or more signals indicative of brain activity of a patient; a stimulation generator configured to generate and deliver electrical stimulation to the brain of the patient that potentiates a favorable brain state of the patient; and control circuitry comprising a processor and memory storing program instructions executable by the processor, the control circuitry configured to detect a favorable brain state episode based on the one or more signals and control delivery of the electrical stimulation within a window of time that extends no greater than 250 milliseconds from occurrence of the favorable brain state episode in response to the detection of the favorable brain state episode, the favorable brain state associated with a decrease in one or more symptoms of a brain condition of the patient.

In various system embodiments, detection of the favorable brain state event by the control circuitry comprises recognition of one or more patterns in the one or more brain signals that correspond to one or more biomarkers stored in memory and indicative of the favorable brain state. In various system embodiments, the control circuitry is configured to detect the favorable brain state episode based on a power level of a frequency band of the one or more signals crossing a threshold. In various system embodiments, the favorable brain state episode comprises the brain transitioning from one brain state to a different brain state. In various system embodiments, the control circuitry is configured to titrate one or more delivery parameters of the electrical stimulation based on increasing the potentiation effect of the electrical stimulation on the favorable brain state. In various system embodiments, the control circuitry is configured to titrate one or more delivery parameters of the electrical stimulation based on increasing one or both of frequency and duration of occurrence of the favorable brain state. In various system embodiments, the control circuitry is configured to titrate one or more delivery parameters of the electrical stimulation based on increasing the amplitude of the one or more signals indicative of the favorable brain state.

In various system embodiments, the control circuitry is configured to identify one or more brain signal biomarkers of the patient as indicative of the favorable brain state and store the one or more brain signal biomarkers in memory, wherein the control circuitry is configured to detect the favorable brain state episode by recognizing presence of the one or more biomarkers in the one or more brain signals. In various system embodiments, the electrical stimulation comprises only one or two pulses delivered within the window of time which is opened for each detection of the favorable brain state. In various system embodiments, the control circuitry is configured to time delivery of the electrical stimulation to coincide with a particular phase of the one or more brain signals from which the favorable brain state episode is detected. In various system embodiments, the window of time spans from the beginning of occurrence of the episode of the favorable brain state and extends no greater than 100 milliseconds from the end of occurrence of the favorable brain state episode. In various system embodiments, the one or more sensors comprise implantable brain electrodes and the one or more brain signals comprise one or more local field potential signals.

Various embodiments concern a system, comprising: means for monitoring one or more brain signals; means for detecting an episode of a favorable brain state based on the one or more brain signals, the favorable brain state associated with a decrease in one or more symptoms of a brain condition of the patient; and means for delivering electrical stimulation that potentiates the favorable brain state to the brain of the patient in response to the detection of the favorable brain state episode, the electrical stimulation delivered within a window of time that extends no greater than 250 milliseconds from occurrence of the favorable brain state episode. Such system embodiments may include any of the options described above.

Various embodiments concern a physically embodied computer-readable medium comprising instructions that cause a processor to: monitor one or more brain signals; detect an episode of a favorable brain state based on the one or more brain signals, the favorable brain state associated with a decrease in one or more symptoms of a brain condition of the patient; and deliver electrical stimulation that potentiates the favorable brain state to the brain of the patient in response to the detection of the favorable brain state episode, the electrical stimulation delivered within a window of time that extends no greater than 250 milliseconds from occurrence of the favorable brain state episode. The physically embodied computer-readable medium may comprise instructions for implementing any of the options described above.

The details of one or more examples are set forth in the accompanying drawings and the description below. Other features, objects, and advantages will be apparent from the description and drawings, and from the claims.

DETAILED DESCRIPTION

Figure 1:
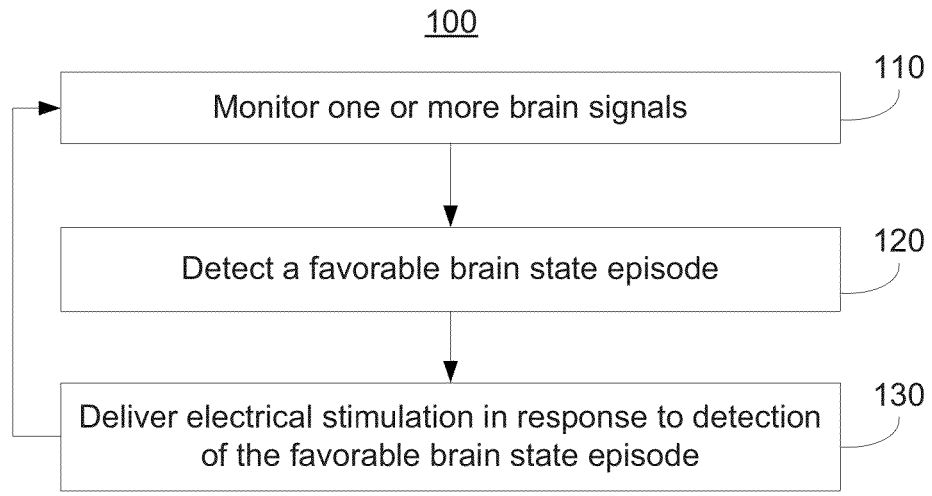
FIG. 1 is a flow diagram for delivering electrical stimulation for potentiating a favorable brain state.

The human brain is composed of billions of neurons electrically interconnected and organized into various areas to perform a variety of functions. The neurons of a particular area can be associated with one or more different brain functions. These areas can share networks of neurons. The electrical activation of neurons is responsible for the function of the brain and communication amongst the various areas of the brain along the networks. It is generally thought that the activation of numerous neurons is necessary to carryout each brain function. Moreover, for various areas of the brain, many of the neurons in one or more areas of the brain will depolarize in synchrony in an effort to carryout a function supported by the one or more areas. The oscillation of brain areas can be measured as a bioelectrical brain signal, such as a local field potential (LFP), electroencephalogram (EEG), and/or electrocorticogram (ECoG) signal, among other measurement techniques. Depending on what functions are being carried out, the brain can operate in a number of different states. Some brain states are symptomatic of disease, such as epileptic patterns associated with seizures or certain oscillatory patterns associated with Parkinson's disease.

Certain neurological and psychiatric disorders can be characterized by deficits in large-scale integration across distributed brain networks. Subsequent to a variety of neurological injuries (e.g., stroke) and diseases (e.g., Parkinson's disease) the normal patterns of neuronal activity can be disrupted, possibility in multiple brain regions, due to cell degeneration and death of neurons or other consequences of injury and disease. Such damage can weaken the connections between brain areas and frustrate the ability of the brain areas to coordinate and carryout normal brain functions. This reduced coordination may compromise functions of the brain requiring distributed networks and/or frustrate the ability of the brain to transition from one task to another. Due to the plasticity of the brain, however, connections between brain areas can be improved to counteract the damage to the brain networks by injury or disease.

This disclosure concerns methods and devices to selectively potentiate functional connectivity in neuronal networks that gives rise to a desired neural activity pattern and/or a desired behavior. Electrical stimulation can be delivered based on identified brain states associated with the desired neural activity pattern and/or other neural pattern. For example, such a method or device may detect a desired brain state associated with an improved patient condition and stimulate in the brain at appropriately selected targets to potentiate these desired patterns. Such a method or device can establish or reinforce desired brain patterns associated with the improved patient condition. Based on brain plasticity, appropriately timed stimulation would lead to potentiation of the stimulated networks, thus allowing the desired state to persist longer and be more easily induced. Because the desired states are associated with improved patient condition, the neural networks and patterns can be established and/or strengthened. Various embodiments of the present disclosure concern delivering electrical stimulation to the brain to improve network connectivity and help restore brain function. In particular, electrical stimulation is delivered to potentiate a favorable brain state as a desired brain state when the favorable brain state is detected as a reinforcement of the networks supporting the favorable brain state.

A favorable brain state, as the term is used herein, refers to a state of activity in the brain of a patient that is associated with decreased symptoms of a problematic brain condition. Favorable brain states can be different depending on the particular disease of which a patient suffers. For example, a 60-80 Hz bioelectrical oscillation as the dominant energy content in the frequency domain of a brain signal may be unremarkable for a patient with no history of Parkinson's disease but may be associated with decreased Parkinson's disease symptoms, such as tremor, in a patient with Parkinson's disease.

Some favorable brain states are not necessarily steady states and include the ability of a brain to transition from one activity or mode to the next. For example, the brain of some people may become stuck in a certain mode, as indicated by unchanging bioelectrical activity (e.g., significant bioelectrical oscillatory activity centered on one frequency for a prolonged duration). Such conditions can inhibit the flexibility of the brain in carrying out the variety of functions which brains can normally do with ease. As such, successful transition from one process to another can be indicative of a favorable brain state in a patient having difficulty engaging various brain areas as needed. In the case of a patient suffering from Schizophrenia, synchrony in bioelectrical oscillations between two areas of the patient's brain may be indicative of a favorable brain state. In various disorders, a brain state indicted by biomarkers may be associated with symptoms of a neurological disorder and an identifiable brain state without those markers and associated with relief from symptoms may be identified as a favorable brain state.

As described herein, various embodiments concern a closed-loop stimulator that delivers stimulation only when certain changes in brain state are detected, such as a change indicative of a favorable brain state (e.g., a desired brain state associated with an improved condition). An objective of therapy can be to make, improve, and/or strengthen neural pathways associated with an improved patient condition as a treatment for brain damage and/or a diseased brain. In various embodiments, whenever a brain state known to be indicative of symptom relief (e.g., decrease in tremors or improved cognition, mood, or motor abilities) is detected, electrical stimulation can be delivered with certain parameters established or calculated to aid the maintenance of that brain state. The electrical therapy may be delivered in the manner of deep brain stimulation (DBS), which is discussed further herein.

A potential advantage of therapy would be that the desired brain state may become a stronger attractor state and hence the brain would endogenously end up spending more time in or around that state associated with decreased symptoms, thus possibly reducing the time the stimulation has to be applied. A related advantage may be that due to the potentiation of a favorable brain state, the stimulation intensity could be reduced, as circuits become more resonant at the desired frequency/patterns of firing and neural elements become more tuned to the desired pattern through reinforcement.

The elements of monitoring, detecting, and delivering therapy as described herein can be applicable to many brain damage and disease states. Monitored and/or stimulated areas may concern the brain and may additionally/alternatively concern other neural networks of the body. Therapeutic applications include, without limitation, delivery of electrical stimulation to potentiate favorable brain states associated with relief from chronic pain, Alzheimer's disease, depression, epilepsy, Parkinson's disease, dystonia, tremor, akinesia, neuralgia, sleep dysfunction, depression, obsessive compulsive disorder, obesity, addiction (e.g., to a drug or activity), gastroparesis, urinary or fecal incontinence, sexual dysfunction or other conditions. Neural targets can include the basal ganglia, cerebral cortex, thalamus, or specific locations within these structures that are implicated in neurological disease.

FIG. 1 illustrates a flow diagram of a method 100 for potentiating favorable brain states. The method 100 includes monitoring 110 one or more brain signals. Monitoring 110 can include receiving one or more signals from the brain, such as EEG, ECoG, LFP, and/or fMRI signals via sensing circuitry. A favorable brain state can be detected 120 based on the one or more monitored 110 signals. An electrical stimulation therapy can then be delivered 130 in response to detection 120 of the favorable brain state. As such, various embodiments of the present disclosure concern delivering 130 electrical stimulation in response to detection 120 of a favorable brain state episode in a manner to potentiate the favorable brain state.

Although the flow diagram of FIG. 1 illustrates monitoring 110 as one of several steps, monitoring 110 can be performed concurrently or intermittently with the other steps of the method 100. Likewise, detection 120 of a favorable brain state may always be attempted as long as monitoring 110 is taking place. The loop of FIG. 1, as well as in the other flow diagrams discussed herein, can be repeated for each of a plurality of occurrences of the favorable brain state, such that a round of therapy (e.g., only one or two pulses, or in some cases more pulses) is delivered for each favorable brain state episode. In some embodiments, electrical stimulation is delivered for the entire duration over which the favorable brain state is detected, or intermittently over the duration.

In the case of Parkinson's disease or other conditions, stimulation targets could be in the motor cortex (Ml), basal ganglia-thalamo-cortical loop, subthalamic nucleus (STN), or the globus pallidus interna (GPi), for example. Beta band frequency oscillations (10 Hz≤β≤30 Hz) and/or gamma band frequency oscillations (50 Hz≤γ≤100 Hz) in the brain can be monitored 110 and power levels characterizing the activity content of each band can be determined. For some patients, high power in the gamma band and/or low power in beta band may be associated with decreased Parkinson's disease symptoms and therefore be indicative of a favorable brain state.

One or more pulses for inducing long term potentiation can be delivered 130 to a targeted brain area in response to detection 120 of the favorable brain state (e.g., detection of high power in the gamma frequency band and/or low power in beta frequency band, such as when the a power level crosses a threshold). In various implementations, each pulse can be phase locked to a peak or other feature of a LFP signal, such that each pulse is delivered following a predetermined duration from the feature. For example, the predetermined duration may be between 10-80 milliseconds, with each pulse being between 50-300 microseconds and having an amplitude within 0.1-6 volts. Other parameters are contemplated, such as higher pulse voltages in treating psychiatric conditions. In various embodiments, a single pulse is delivered for each detection of a favorable brain state (i.e. each episode), up to 500 Hz when instances of the favorable brain state are detected that quickly. In this way, each episode of a favorable brain state may be extremely short such that several episodes can occur within a second. In various embodiments, stimulation is delivered for some ratio of favorable brain state detections, such as delivering a single pulse for one of every three detections of an indicator of the favorable brain state.

In some embodiments, a change in the power level of a frequency band of a sensed brain signal may indicate a favorable brain state and trigger electrical stimulation. For example, when a drop in the beta frequency band power is detected in Parkinson's disease patients as a favorable brain state, stimulation can be delivered to promote the favorable brain state. In some embodiments, when an increase in the gamma frequency band power is detected in Parkinson's disease patients as a favorable brain state, stimulation can be delivered at parameters known or thought to increase gamma frequencies. In some cases, the favorable brain state triggering the delivery of one or more pulses will be the transition of frequency content in and/or out of the gamma frequency band, which is suggestive of brain flexibility.

Electrical stimulation can reinforce and strengthen brain networks that support this favorable brain state, thereby making it easier for the brain to transition into and sustain the favorable brain state. In some cases, electrical stimulation in response to favorable brain states can amplify existing electrical connections and/or increase the number of new connections, as neurons tend to create and strengthen connections between simultaneously activated neurons. In some embodiments, therapy response may be a stimulus to evoke single spikes in a neuron, bursts of stimulation, or a train of stimulation pulses following the detection of a favorable brain state or improved condition. In some cases, other connections to or from the target that may not be directly involved in the maintenance of the favorable brain state may not be potentiated as the stimulus may not be paired in a temporal manner with them, and hence the effects of stimulation may be specific to the directly functionally correlated areas and neurons. Use of a window or other timing requirement temporally pairing the favorable brain state episode to one or more pulses of electrical stimulation can help selectively potentiate the favorable brain state while avoiding the potentiation of other brain states and/or other brain networks. Delivering electrical stimulation too long after a favorable brain state episode not only misses the opportunity to potentiate the favorable brain state but risks reinforcing a non-desirable brain state.

Figure 2:
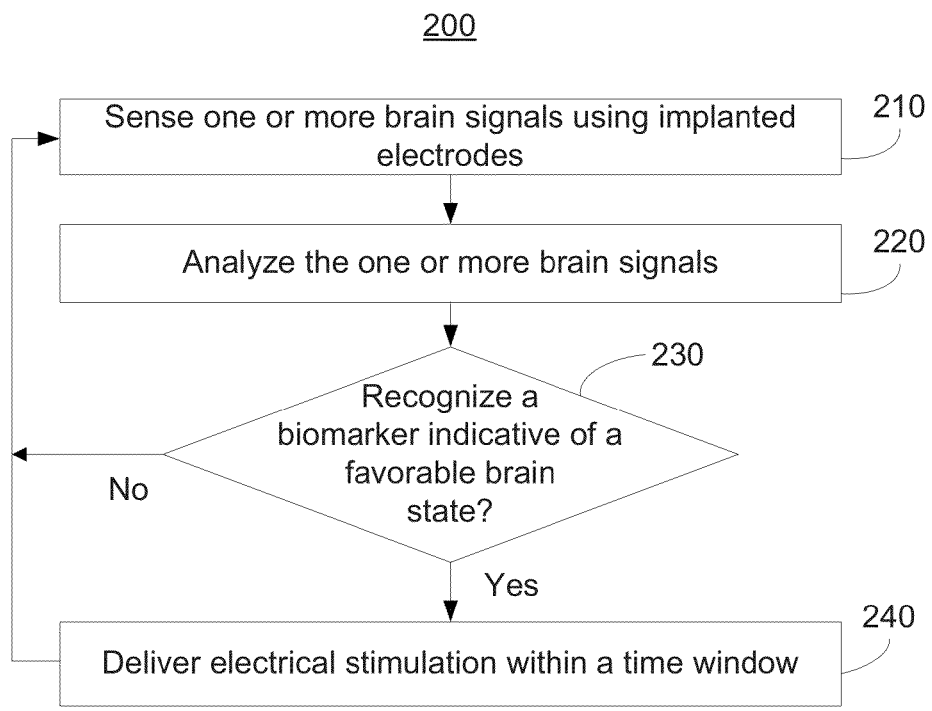
FIG. 2 is a flow diagram for delivering electrical stimulation for potentiating a favorable brain state.

FIG. 2 illustrates a flow diagram of a method 200 for potentiating favorable brain states. The method 200 of FIG. 2 can be implemented in the same embodiments as the method 100 of FIG. 1 with the respective flow diagrams highlighting different aspects of potentiating favorable brain states. As shown in FIG. 2, the method 200 includes sensing 210 one or more brain signals using implanted electrodes. The electrodes can be implanted on the surface of a brain or deeper within the brain on a lead. The signals can be carried by conductors to control circuitry, which can include amplifiers, measurement circuits, and discriminating circuits. Control circuitry can analyze 220 the one or more signals to determine whether a biomarker indicative of a favorable brain state can be recognized 230.

A favorable brain state can be recognized by a neural signature or biomarker. A favorable brain state may be recognized based on a sensed frequency, bioelectrical oscillation frequency power, phase of oscillation, and/or synchronization (or non-synchronization) with another area of the brain, for example. A favorable brain state can be detected in terms of firing rate of a single cell or groups of cells. A favorable brain state can also be detected in terms of oscillations in the LFP recordings.

A biomarker, as referred to herein, is a characteristic of one or more signals that indicates the presence of a particular brain state, such as a favorable brain state. For example, a biomarker may be a relatively high level of frequency content of electrical brain oscillations centered on a frequency associated with a particular brain state. In this example, the brain state may be favorable brain state because it is associated with decreased disease symptoms compared to other brain states. In the case of a Parkinson's disease patient, a favorable brain state may be associated with decreased tremor and/or other symptoms of Parkinson's disease and a relatively high bioelectrical frequency power level around 70 Hz in the frequency domain. As such, a power level threshold may be set at this frequency as a biomarker where above the threshold a favorable brain state is indicated. Because this brain state is associated with lesser Parkinson's disease symptoms, it can be desirable to have the patient in this favorable brain state more often and for longer durations. As such, electrical stimulation is delivered 240 within a time window temporally associated with an episode of occurrence of the favorable brain state.

In various embodiments of the present disclosure, as in the method 200 of FIG. 2, all pulses of the potentiating electrical stimulation are delivered 240 within a window of time that is based on the favorable brain state event, such as the end of the favorable brain state episode. For example, in some embodiments, the electrical stimulation is delivered 240 within a time window that extends no further than 100 milliseconds past the end of a detected favorable brain state episode, the end of the favorable brain state episode being defined as the time at which the biomarker no longer indicates the occurrence of the favorable brain state. In some embodiments, the electrical stimulation is delivered 240 within a time window that extends no further than 50 milliseconds past the end of the favorable brain state episode. Other time window values are also contemplated, such as 250 and 20 milliseconds, and durations in between. The electrical stimulation is temporally associated with the occurrence of the favorable brain state (e.g., through use of a window) so that the network(s) supporting the favorable brain state are reinforced when activated or just activated, and not other networks that do not support, or are antagonistic with, the favorable brain state. Waiting too long upon recognition of a favorable brain state risks delivering reinforcing stimulation when the favorable brain state has passed and further when a different network is activated. As such, a time window can be used to temporally correlate the electrical stimulation to the favorable brain state.

In some embodiments, electrical therapy will only be delivered if it can be determined that the electrical stimulation will be delivered when the favorable brain state is active. In such embodiments, if it is recognized that a favorable brain state has ended before therapy can be delivered, such as in the case of a particularly short episode, the electrical stimulation will not be delivered. However, in some other embodiments, stimulation will be delivered in association with an episode of a favorable brain state even if the favorable brain state has ended. A time window can be used to deliver electrical stimulation for a particular episode of a favorable brain state during or after the favorable brain state, the later limit of the window ensuring that the electrical stimulation is not delivered too long after the end of the favorable brain state where it has little or no effect in potentiating the favorable brain state. For example, a window can be set for each favorable brain state episode detected, the window spanning from the beginning of the episode (or at the time the episode is first detected) to some time after the episode has ended (e.g., 50 milliseconds). A countdown timer can be started when it is determined that the episode has ended to determine when the window ends and delivery 240 of the electrical stimulation will no longer be allowed. For example, if stimulation is only allowed up to 20 milliseconds from when the favorable brain state episode ends, then a countdown timer will start at the detected end of the favorable brain state episode, and stimulation for the episode will not be allowed following expiration of the timer.

In some embodiments, the therapy delivery protocol requires that the electrical stimulation be delivered following a predetermined delay from some feature of the favorable brain state episode, such as the end of the favorable brain state episode. For example, if the delay is 20 milliseconds, then a countdown timer will be started when the end of the favorable brain state episode is detected (e.g., when the biomarker no longer indicates that the favorable brain state is occurring), and the electrical stimulation will be delivered at the expiration of the 20 millisecond delay.

In some embodiments, as many pulses as can be delivered at a certain frequency will be delivered within the window as long as it is open. Therefore, if the window extends 100 milliseconds from the end of a favorable brain state episode, then a plurality of pulses will be delivered at some frequency until the window closes. In some embodiments, only a limited number of pulses will be delivered within the window (e.g., one, two, ten, or some greater number) and the delivery of the pulses will end for that favorable brain state event when either the limited number of pulses is delivered or the window closes, which ever happens sooner.

Although the flow diagram of FIG. 2 illustrates sensing 210 as one of several steps, sensing 210 can be performed concurrently or intermittently with the other steps of the method 200. Likewise, analysis 220 of the one or more brain signals and an attempt to recognize a biomarker indicative of a favorable brain state 230 can take place as long as sensing 210 is taking place. In some embodiments, blanking in sensing 210 can be used to allow sensing 210 of bioelectrical signals without concurrent electrical stimulation delivery 240.

Figure 3:
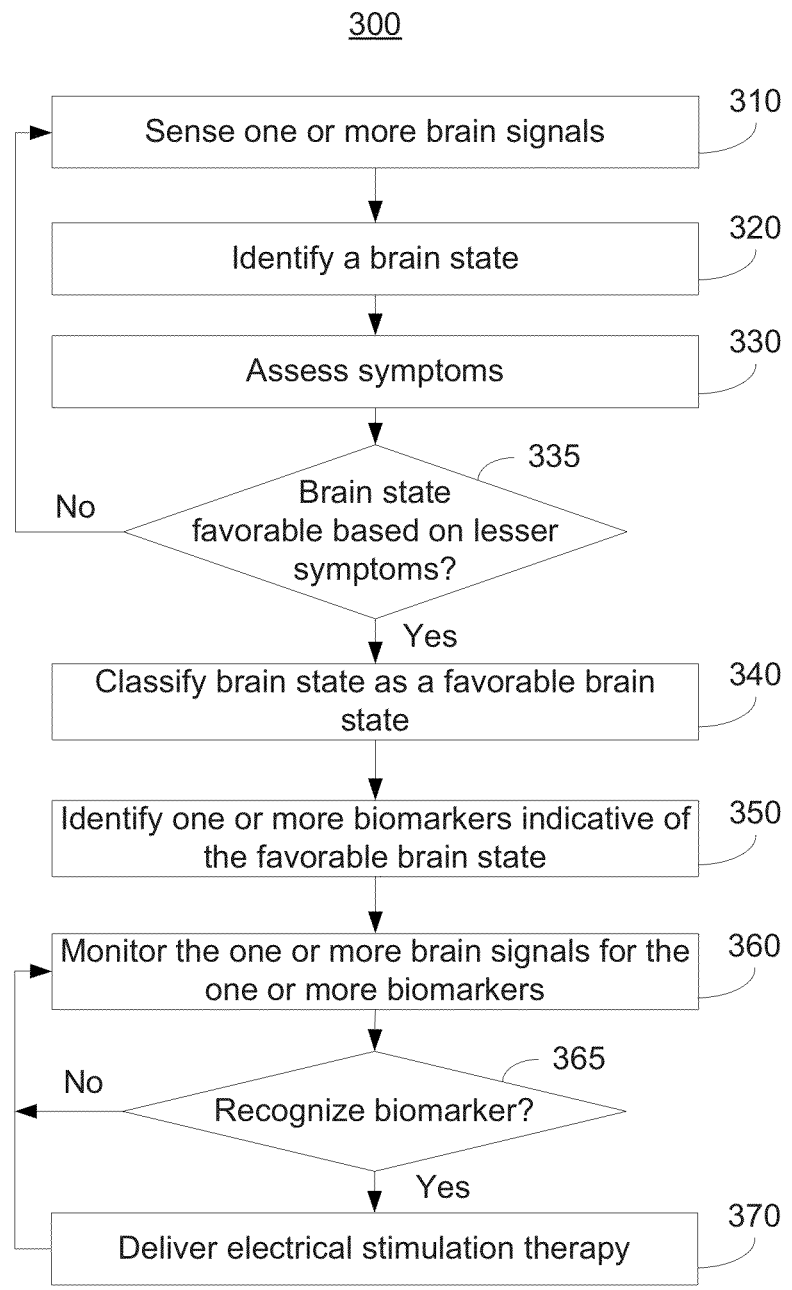
FIG. 3 is a flow diagram for identifying a favorable brain state and potentiating the favorable brain state.

FIG. 3 illustrates a flow diagram of a method 300 for potentiating favorable brain states. The method 300 of FIG. 3 can be embodied together with the method 100 of FIG. 1 and/or method 200 of FIG. 2 with the respective flow diagrams highlighting different aspects of potentiating favorable brain states. The flow diagram of FIG. 3 highlights, among other things, determining which brain states are favorable and how those brain states can be distinguished.

The method 300 of FIG. 3 includes sensing 310 one or more brain signals, which can be performed in any manner referenced herein. From the one or more sensed 310 brain signals, a brain state can be identified 320. Such identification 320 can be performed by looking for patterns that emerge in the one or more signals, such as energy content within a particular bioelectrical frequency band, morphological patterns, consistent period of oscillation, synchronization with another brain area, and/or changes in bioelectrical oscillation frequency, and/or changes in bioelectrical amplitude, for example.

In some cases, predetermined patterns are stored in memory as common signatures of various brain states and the one or more signals can be checked for the presence of the one or more predetermined patterns. Each of the predetermined patterns may be based on clinical data and may already be associated with particular brain states.

The method 300 also includes assessing 330 symptoms. The assessed 330 symptoms may be symptoms associated with an identified 320 brain state. In various embodiments, once a brain state is identified 320, particular symptoms associated with the brain state are then assessed (e.g., if low frequency bioelectrical oscillations are identified then an assessment 330 of Parkinson's disease symptoms, such as tremor via an accelerometer, can be performed).

Based on the assessment 330 of symptoms, it is determined whether the identified 320 brain state is a favorable brain state 335. An identified 320 brain state may be determined to be a favorable brain state 335 if the brain state is associated with fewer symptoms. For example, if fewer symptoms are exhibited during the same time the patient is in the identified 320 brain state, then the brain state may be determined to be a favorable brain state 335. In some cases, the diminishment in symptoms may be experienced following the identified 320 brain state and in which case a lower incidence of symptoms with an increased presence of the identified 320 brain state over time may determine that the identified 320 brain state is a favorable brain state 335. A lower incidence of symptoms may be determined by comparing the assessment 330 of symptoms during the identified 320 brain state to symptoms logged (e.g., using the same symptom assessment 330 technique) when the patient was not in the identified 320 brain state.

If the identified 320 brain state is determined to not be a favorable brain state 335 based on a lack of association with decreased symptoms, then the method 300 can continue to sense 310 one or more brain signals and test another identified 320 brain state in the same manner. In such a case, a different brain state signature can be used so that a different brain state can be tested.

When an identified 320 brain state is determined to be associated with decreased symptoms and therefore a favorable brain state 335, then the brain state can be classified 340 as a favorable brain state. Classifying 340 a brain state as a favorable brain state may include making a record in memory of an association between the identified 320 brain state and the diminished symptoms, and may include saving discriminating data (e.g., a threshold or biomarker) for detecting the favorable brain state in memory.

For each classified 340 favorable brain state, one or more biomarkers indicative of the favorable brain state can be identified 350. The identified 350 biomarkers may be the same biomarkers that were used to identify 320 the brain state. In some embodiments, the identified 350 biomarkers may be a refined version of the same biomarkers that were used to identify 320 the brain state. For example, a predetermined frequency range may be used to first identify 320 brain states as candidates for a favorable brain state based on the power level of a signal and then further discrimination of the classified 340 favorable brain state may narrow the frequency content range for a particular patient when it is better understood for that patient at which frequency the patient's brain exhibits oscillation when in the favorable brain state. Likewise, a generic morphology may be used to first identify 320 brain states as candidates for a favorable brain state and then further discrimination of classified 340 favorable brain states may be used to establish specific or customized signatures of the favorable brain state, such as refined morphology templates or thresholds. Indentifying 350 the one or more biomarkers may include setting a favorable brain state threshold.

The identified 350 one or more biomarkers indicative of the favorable brain state may be used in monitoring 360 the one or more signals. For example, if the biomarkers comprise frequency content bands or morphologic discriminators, then the one or more signals can be analyzed for the presence of these biomarkers. If a biomarker is recognized in the one or more signals 365, then electrical stimulation can be delivered 370 in response to the recognition of the biomarker. Sensing 310 of the one or more signals and delivery 370 of the electrical stimulation, as well as the other processes of the method 300 of FIG. 3, can be performed in any manner referenced herein.

Although the flow diagram of FIG. 3 illustrates sensing 310 as one of several steps, sensing 310 can be performed concurrently or intermittently with the other steps of the method 300. Likewise, the other steps of the method 300 can be performed concurrently or intermittently with the other steps of the method 300 in various embodiments regardless of the sequence with which they are presented in the example of FIG. 3.

In some embodiments, a patient may indicate a desired behavioral state (e.g., symptom relief, such as improved mood for a person suffering from deep depression or decreased need for a substance or activity to which the patient is addicted) by pressing a button on an actuator when the patient observes an improved condition. In the case of a Parkinson's disease patient, the patient may provide an input when he or she is able to perform a motor function in an easier than expected manner. When an input indicating an improved condition is made, a device can then sense and record one or more brain states of the patient. Based on this record, or multiple records for multiple instances, a desired brain state pattern may be recognized and associated with the improved condition as a favorable brain state. Such use of a button or other input for highlighting times when the patient recognizes an improved condition to facilitate focus on corresponding brain states can be employed in identifying 320 a brain state and assessing 330 symptoms. For example, identifying 320 the brain state and assessing 330 symptoms may be triggered by the patient or clinician when relief in symptoms is observed. An implanted device can then monitor 360 one or more brain signals and deliver 370 stimulation upon recognition of the desired brain state to reinforce the desired brain state. Further monitoring 360 can then track frequency of occurrence of the desired brain state as well as the improved condition to provide further feedback on efficacy of the therapy. In this example, such patient-triggered episodes of improved condition may be used to build a template (e.g., as a discriminating biomarker) or database of signals that should be potentiated as a favorable brain state, as in the process of identifying 350 a biomarker. Thus, for example, a patient may press a button on a patient programmer to trigger loop recording for a certain amount of time when the patient feels that he or she is in a preferable condition (e.g., reduced symptoms). The recorded signal can then be stored on the device temporarily and then downloaded for offline storage and processing to recognize a favorable brain state pattern. Such recognition could also be performed by an implanted device. The recognized brain state can then be used to trigger electrical stimulation when it is subsequently detected.

A favorable brain state threshold can be developed for a particular patient as a biomarker. The favorable brain state threshold can then be used to determine when a brain enters into a favorable brain state, such as by a processor of control circuitry comparing a currently measured value to a stored threshold. The processor can analyze a change in one or more signals that is associated with the favorable brain state and set a favorable brain state threshold based on the amount of change (e.g., half or two thirds of the amount of change amount). For example, if an increase in power of a signal in a particular frequency band in the frequency domain is associated with a favorable brain state, then a power level threshold can be set using the power level increase. In some embodiments, the favorable brain state threshold can relate to a change in the dominant frequency at which a brain area is oscillating, such as change greater than 10 Hz. Such setting of a favorable brain state threshold can correspond to the identifying 350 step of the method 300 of FIG. 3.

Determining a favorable brain state threshold can be useful when a brain area typically has low intensity and/or intermittent markers of the favorable brain state even when the patient is not actively in the favorable brain state. However, a brain area may then have a large increase or change in activity when the patient transitions to the favorable brain state. The increase may be quantized and then a point selected within the increase as threshold indicating the transition into a favorable brain state. For example, if there is usually a low level of low frequency oscillatory activity in a brain area when the patient is not in the favorable brain state, and the level of low frequency oscillatory activity increases substantially in power when the patient is in the favorable brain state, then the favorable brain state threshold can be set within this range, such as one half or two thirds of the power range of activity increase. A favorable brain state threshold for other parameters can likewise be set, such as for amplitude, frequency, and phase of bioelectrical brain signals, among others. The setting of a favorable brain state threshold as a biomarker can facilitate an automated detection of a favorable brain state, such as detection of the favorable brain state by a processor of control circuitry that then triggers electrical stimulation.

Figure 4:
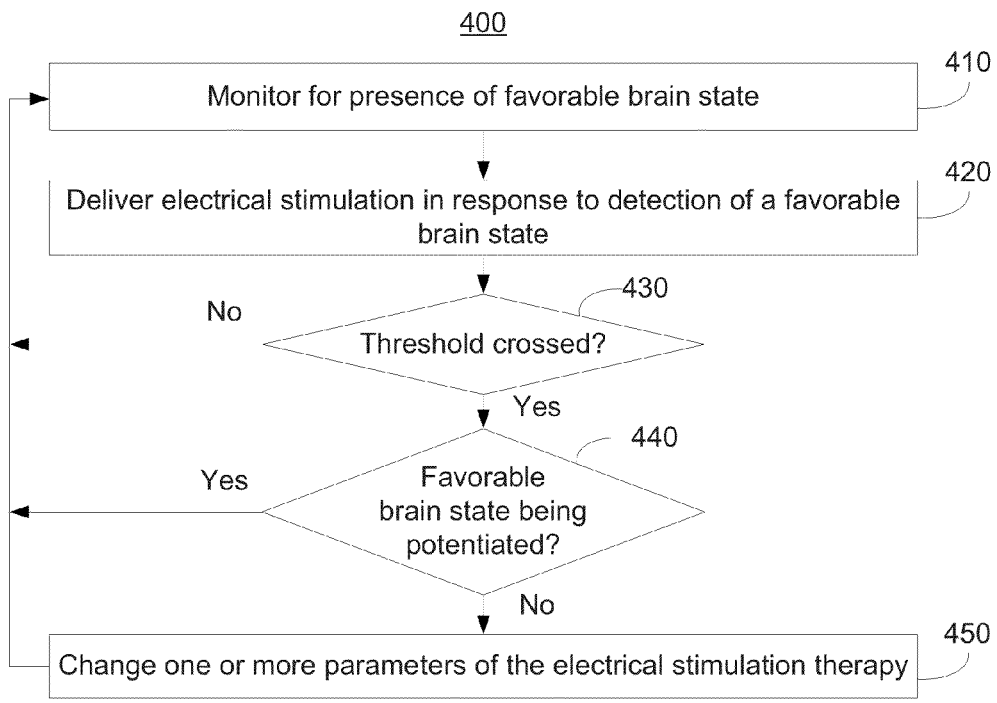
FIG. 4 is a flow diagram for titrating electrical stimulation parameters for potentiating a favorable brain state.

It may be observed that at the outset of therapy the amplitude of the signal evidencing the favorable brain state (e.g., recognized by frequency) was 3 mV but that after some time of therapy delivery the signal showing the same frequency pattern of the favorable brain state is at 5 mV, showing a strengthened association with the favorable brain state by increased intensity of the signal. Such evidence of strengthened association can be used to titrate therapy one or more therapy parameters, such as setting an effective delay between sensing and therapy and/or to validate other aspects of the therapy, such as success of potentiation. For example, increasing intensity of the signal indicating the favorable brain state following administration of the therapy can indicate that the stimulation parameters are likely effective in potentiating the favorable brain state. As such, the intensity of the signal indicating the favorable brain state may be used to titrate stimulation parameters. Improved cognitive and/or motor function can also indicate therapy effectiveness and validate the parameters of the therapy. FIG. 4 further demonstrates aspects of therapy titration.

FIG. 4 illustrates a flow diagram of a method 400 for potentiating a favorable brain state. In particular, the flow diagram of FIG. 4 concerns titrating electrical stimulation parameters to improve potentiation of the favorable brain state. The method 400 of FIG. 4 can be implemented in the same embodiments as the methods of FIGS. 1-3, with the respective flow diagrams highlighting different aspects of potentiating favorable brain states.

The method 400 includes monitoring 410 for the presence of a favorable brain state. Monitoring 410 may be performed in any manner disclosed herein, including by employing the techniques disclosed in association with FIG. 1-3. Favorable brain state episode data may be stored in memory or otherwise logged. For example, for each detection of a favorable brain state episode, a data entry may be made indicating the detection of a favorable brain state episode, the duration of the favorable brain state episode, an indicator of the strength or intensity of the favorable brain state (e.g., amplitude of the LFP signal indicating the favorable brain state), and/or any other metric characterizing the favorable brain state.

The method 400 further includes delivering 420 electrical stimulation in response to detection of a favorable brain state. Delivery 420 of the electrical stimulation can be performed in any manner referenced herein, including by employing the techniques disclosed in association with FIG. 1-3. The delivery 420 step may represent stimulation in response to each of a plurality of favorable brain state episodes over time as a preferred implementation of the method 400 counts the number of delivery 420 episodes and/or time during which delivery 420 was available. The threshold check 430 can determine whether electrical stimulation was delivered 420 for a threshold number of episodes of occurrence of a favorable brain state, such as 100 episodes of detection and stimulation. Alternatively, or additionally, threshold check 430 can determine whether a predetermined amount of time has passed during which monitoring 410 continued and electrical stimulation delivery 420 was available, such as 10 days.

An assessment of potentiation 440 can be performed using the data collected while monitoring 410 the favorable brain state to assess the efficacy of the parameters used to deliver 420 the electrical stimulation. It is understood that potentiation of a favorable brain state may take time, as in some cases success of the therapy may result from structural changes in the brain in response to the therapy. An assessment can be performed to determine whether a favorable brain state is being potentiated 440 after the threshold is crossed 430. The potentiation assessment 440 may measure the frequency of occurrence of the favorable brain state, measure the duration of the episodes (e.g., average duration, median duration, variability of duration, or standard deviation of duration), intensity of the episodes (e.g., amplitude of the signals indicating the favorable brain state or a measure of signal power or strength of the signals), or other measure that can assess the relative presence of the favorable brain state. The measure of the favorable brain state can then be compared to a threshold or historical value, such as a comparable measure of the favorable brain state without electrical stimulation or with different electrical stimulation parameters. In some implementations, monitoring 410 is performed for a time (e.g., hours or days) before electrical stimulation is available to be delivered 420 so that a baseline measure of presence of the favorable brain state can be made (e.g., how frequently the favorable brain state occurs or the average favorable brain state duration without electrical stimulation attempting to potentiate the favorable brain state). In such cases, a comparison can be performed between the measure of the presence of the favorable brain state with and without delivery 420 of electrical stimulation to determine whether the favorable brain state is more frequent, longer in duration, or more intense with therapy.

If the check of the favorable brain state potentiation 440 determines that the favorable brain state is being potentiated (e.g., by the episodes of the favorable brain state being more frequent, longer in duration, and/or having higher signal amplitude) then the electrical stimulation delivery 420 can continue using the same parameters. In some embodiments, a threshold level of improvement must be recognized in order for a determination to be made that the favorable brain state is being potentiated 440 (e.g., episodes are 25% more frequent or have a 25% increase in duration) and indicate further usage of the stimulation parameters unchanged. In some implementations, the check of the favorable brain state potentiation 440 can qualify the current stimulation parameters as effective in potentiating the favorable brain state and trigger an output on a display indicating that the electrical stimulation parameters are effective. Qualifying the current stimulation parameters can include setting the current stimulation parameters as therapy deliver parameters used in subsequent therapy administration.

If the check of the favorable brain state potentiation 440 determines that the favorable brain state is not being potentiated (e.g., by the episodes of the favorable brain state not being more frequent or longer in duration) or not being potentiated enough based on threshold (e.g., less than 25% increase in frequency or duration), then one or more parameters of the electrical stimulation delivery 420 can be changed 450 and the method 400 continued with the revised parameters.

Changing 450 one or more parameters can include changing the energy level of the electrical therapy, such as by adjusting frequency, amplitude, and/or duration of one or more pulses comprising the electrical therapy. Other parameters that can be changed 450 include adjusting the timing of an electrical stimulation window or other timing parameter for delivery of electrical stimulation. For example, a delay between detection of a favorable brain state, a feature of a favorable brain state (e.g., peak amplitude), or the end of a favorable brain state episode, and delivery of one or more pulses may be increased or decreased as a parameter change 450. In various embodiments, the changed 450 parameter is the timing of electrical stimulation relative to bioelectrical oscillatory characteristics of the favorable brain state, such as the phase or period of the oscillatory activity. In some cases, a lead may be advanced or retracted within the brain as a parameter change 450 until an optimal electrode position is found for potentiation. Electrode combinations for delivering 420 the electrical stimulation can also be changed 450 until a satisfactory electrode combination is found for potentiating the favorable brain state.

As such, the techniques of the method 400 of FIG. 4 can scan through therapy parameters to identify appropriate configurations that provide for efficacious stimulation. Various embodiments can collect and store historical values and outcomes from favorable brain state potentiation 440 test in memory, such that it is unnecessary to scan in certain ranges when it can be recognized (e.g., by a processor of control circuitry) that a parameter configuration, or one close to it, has already been tested. Such automatic recognition can be useful so that a parameter scan does not return to a configuration already tested. For example, if a previous test indicated that stimulation of 6 volts failed to cause potentiation of the favorable brain state, then a subsequent upward voltage scan can be stopped before it reaches, or approaches, the 6 volt level. In such a case, a different parameter may be changed than the one already used in the scan, such as pulse width, phase lock delay and/or electrode combination, either automatically or manually.

Various embodiments can include extended monitoring and tracking the occurrence of a favorable brain state to determine whether the episodes are becoming more frequent (e.g., episodes per hour, day, week), longer, and/or stronger (e.g., intensity of biomarkers). Tracking a favorable brain state to determine whether it is being potentiated 440 may include determining the duration of the occurrence of the favorable brain state. The duration of an episode may be measured from the time some measure of the favorable brain state (e.g., power level of a certain bioelectrical oscillation frequency) rises above a threshold (e.g., a predetermined amount previously associated with the transition to the favorable brain state) to the time that the measure falls below the threshold. Characterizing the incidence of a favorable brain state may include determining the duration of a favorable brain state and/or the total time over a period of time that the patient's brain is in the favorable brain state (e.g., minutes per day). An output of a device can be made based on characterizing the incidence of the favorable brain state, such as an indication of a display. Such characterization can be used to track the efficacy of therapy and assess whether the brain state is being potentiated, with greater time spent in the favorable brain state indicating an improving condition and potentiation.

In various embodiments, a test, such as favorable brain state potentiation 440 test, can determine that a favorable brain state is being successfully potentiated or has been successfully potentiated. In such a case, the therapy can be scaled back or discontinued, such as by reducing an energy delivery parameter, decreasing the frequency of pulse delivery, and/or implementing a maintenance stimulation protocol. For example, if the favorable brain state is detected to occur at a threshold level, such as 100 times a minute, and the present indicator of the favorable brain state has an amplitude above a threshold level, or the favorable brain state is generally present for a threshold percentage of time (e.g., 20% of the time over a 12 hour period), then a change in delivery can be made. The change may comprise decreasing the frequency of delivery (e.g., delivering a single pulse for every third detection of the favorable brain state instead of for every detection), decreasing pulse amplitude and/or width, or changing some other parameter that decreases the overall therapy burden.

The use of a minimum favorable brain state duration threshold may be used to qualify an episode of a favorable brain state for identification, tracking of a condition, and/or controlling a therapy. For example, an occurrence of a favorable brain state may not count as an episode of a favorable brain state for the purpose of identifying an episode of a favorable brain, assessing potentiation, and/or triggering electrical stimulation until the episode persists for a predetermined period of time (e.g., a threshold within 2-5 seconds), because short periods of indication of a favorable brain state may not evidence meaningful transition into a favorable brain state. In various embodiments, no electrical stimulation will be delivered until indicators of the favorable brain state persist for the threshold duration, and then one or more pulses can be delivered for each subsequent indicator detected (e.g., each signal peak) until consistent indicators are no longer detected for some time (e.g., a threshold within 2-5 seconds).

An element to inducing potentiation of a favorable brain state may be timing one or more pulses relative to ongoing oscillatory activities. For example, the timing of the stimulation may have to be within a certain time window aligned to a particular aspect of the oscillations in the recording target (e.g. the peak of the wave). The time window can be determined based on acute effects of such stimulation. For example, a window following sensed brain oscillatory peaks of a certain brain pattern (e.g., 65 Hz oscillation) may be set based on an increase in amplitude over time (e.g., 5 mV) of the brain signal following stimulation of the area of the brain within the window when the signal shows the certain brain pattern (e.g., 65 Hz). In some cases, a suitable window will be one that enhances the synchrony in the gamma frequency band or establishes neural states and therapeutic benefit to a patient. For example, a patient might suffer a stroke and therefore have cognitive and/or motor function difficulties. However, when one or more certain areas of the brain are monitored by sensing an electrical signal of the area(s) oscillating at 65-90 Hz (the areas may be associated with the diminished cognitive or motor function), the patient may be observed to have improved cognitive and/or motor function, while 20-35 Hz oscillation is associated with especially poor function. A device programmed accordingly can then sense to recognize this 65-90 Hz brain state for this area(s) of the brain and then stimulate the one or more areas, or a different area based on the sensing of the brain state.

Sensing may be performed in one area of the brain and the stimulation may be performed in a different area of the brain (e.g., a networked downstream structure of the brain). A device can then stimulate an area of the brain (the same area that the brain state signal was sensed or a different area) using a predetermined or calculated delay. The delay may be in a window or calculated such that the stimulation is not too temporally separated from the occurrence of the desired brain state but not too close either. Separation in time can be desirable when sensing in one area of the brain and stimulating in another—the separation based in part on the time it would take the signal associated with the desired brain state to reach a diseased/damaged areas (or surrounding area) of the brain or the area targeted for stimulation delivery. In some embodiments, a delay may be at least 50 milliseconds based on the distance between the sensing area and the stimulation area, the time calculated to correspond to the intrinsic conduction time in the brain. Delays between sensing and stimulation may be variable within the range of 1-200 milliseconds, for example. The delay can also take into account observed therapy efficacy. For example, it may be observed that a 60 milliseconds delay is effective to potentiate functional connectivity as evidenced by increased incidence or strengthening of the desired brain state, while a 120 millisecond delay was not. In this case, a delay between sensing of a desired brain state and/or peaks of a signal and pulse delivery can be set for continued therapy delivery at or close to 60 milliseconds.

As described herein, the delay between a favorable brain state event (e.g., moment of recognition or peak amplitude of brain signal indicating the favorable brain state) and one or more stimulation pulses can be titrated to adjust the therapy. Other parameters of brain stimulation can also be titrated to improve potentiation as evidenced, for example, by improved patient condition and/or strengthening of the brain state signal (e.g., strength indicated by signal amplitude). The delay as discussed herein can be a phase shift between the sensed brain state signal and pulse delivery for one or more sinusoidal cycles of the brain state signal or brain event. The flow diagram of FIG. 5 further discusses some of these aspects.

Figure 5:
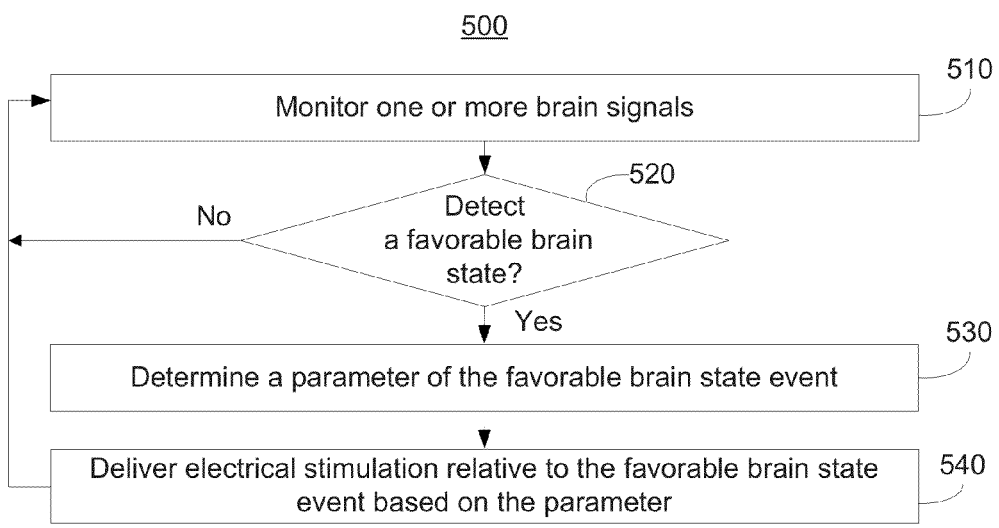
FIG. 5 is a flow diagram for timing delivery of electrical stimulation for potentiating a favorable brain state.

FIG. 5 illustrates a method 500 for potentiating a favorable brain state, and in particular, timing electrical stimulation relative to a characteristic of the favorable brain state. The method 500 of FIG. 5 can be implemented in the same embodiments as the methods of FIGS. 1-4, with the respective flow diagrams highlighting different aspects of potentiating favorable brain states.

The method 500 includes monitoring 510 one or more signals indicative of a favorable brain state. Monitoring 510 may be performed in any manner referenced herein, including in accordance with the techniques discussed in association with FIG. 1-4.

Based on the one or more monitored 510 signals, a favorable brain state can be detected 520. A parameter of the favorable brain state can be determined 530. In some embodiments, the parameter of the favorable brain state is determined 530 in response to the detection 520 of the favorable brain state. In some other embodiments, the parameter of the favorable brain state is determined 530 at all times regardless of whether a favorable brain state is presently detected 520, such as an on-going part of monitoring 510. In such a case, a phase or period of a oscillatory brain signal may be the parameter which is determined 530 at all times during monitoring 510, but a favorable brain state may only be detected 520 when the oscillatory brain signal has significant activity within a certain frequency band or otherwise evidences a biomarker associated with the favorable brain state.

The determined 530 parameter may be, for example, the timing of the end point of the brain state episode or the period of time during which the favorable brain state episode is occurring. In some embodiments, the determined 530 parameter may be the phase, period, or signal peak timing of the bioelectrical oscillatory activity used to detect the favorable brain state 520. The determined 530 parameter may then be used for timing delivery 540 of the electrical stimulation relative to the favorable brain state event. For example, if the electrical stimulation is to be delivered 540 within a time window extending not more than 250 milliseconds from the end of the favorable brain state episode, then a time window can be based on the determined 530 parameter (e.g., the time window may open at the end of the favorable brain state episode). In some embodiments, the time window within which the electrical stimulation is delivered 540 is 50 milliseconds. Delivering 540 the electrical stimulation relative to the favorable brain state event based on the parameter may include timing each pulse relative to the parameter, such as delivering each pulse timed with a phase of oscillatory brain activity, delay following the favorable brain state event, or delay from a feature of the oscillatory brain activity.

Because favorable brain states can be associated with oscillatory characteristics, it may be desirable to deliver pulses relative to the oscillatory characteristics for potentiating the favorable brain state. Therefore, in some embodiments, determining 530 a parameter of the favorable brain state event comprises determining a parameter of the oscillatory pattern of the favorable brain state. For example, if a favorable brain state exhibits a particular oscillatory pattern, then delivery 540 of each pulse could be timed to coincide with a particular phase of the oscillatory pattern, such as the up slope, peak, down slope, or trough of the oscillatory pattern in the time domain. In various embodiments, a pulse may be delivered relative to the time at which the power level of a frequency band in the frequency domain of a brain signal crosses a threshold (e.g., at that time or after a predetermined delay). Depending on the favorable brain state, potentiating the favorable brain state may be more efficacious if the brain state is stimulated in some phase of the oscillatory pattern.

Brain areas targeted for sensing and/or stimulation can be selected based on the pathology of the disease or brain damage of the patient. The targets may be, for example, areas known to support damaged brain areas or areas that can replace the function of damaged brain areas. In some cases, fMRI (functional magnetic resonance imaging) can be used to identify the activation of a brain area supporting a favorable brain state. fMRI can further be used to determine affected areas of the brain that could benefit from the techniques disclosed herein, such that one area can be selected for brain sensing and an associated area can be selected for stimulation. fMRI can map brain activity to a 2D or 3D plot (e.g., on a computer display) allowing activated brain areas to be identified, usually indicated by being colored or otherwise highlighted on a display. While fMRI is used as an exemplar in this disclosure, all other types of neural imaging are contemplated to be used in the same way.

As an example, a patient can be placed in a fMRI field while symptoms of a brain condition are observed, such as by using an accelerometer or measure of tremor or asking the patient to make an assessment of symptoms. An fMRI device display can light up to indicate which area(s) of the brain showed increased activity correlated in time to symptom relief. Such a technique can identify which areas support the favorable brain state. These areas can then be targeted for monitoring for occurrence of the favorable brain state and/or therapy delivery.

In various embodiments, electrical therapy is delivered directly to brain areas targeted for increasing the strength and incidence of the favorable brain state by locating an electrode within a targeted area and using the electrode as an cathode or anode during delivery of electrical energy, such as in the form of one or more pulses. In some cases it may be preferable to directly stimulate an associated brain area (e.g., remote from the targeted area) in an effort to bring about a change in a targeted area (e.g., the areas characterized by insufficient incidence of the favorable brain state). In such cases, the targeted area may be electrically "down stream" from the associated brain area, such that it is more effective and/or safer to electrically treat the targeted area remotely than directly.

Figure 6:
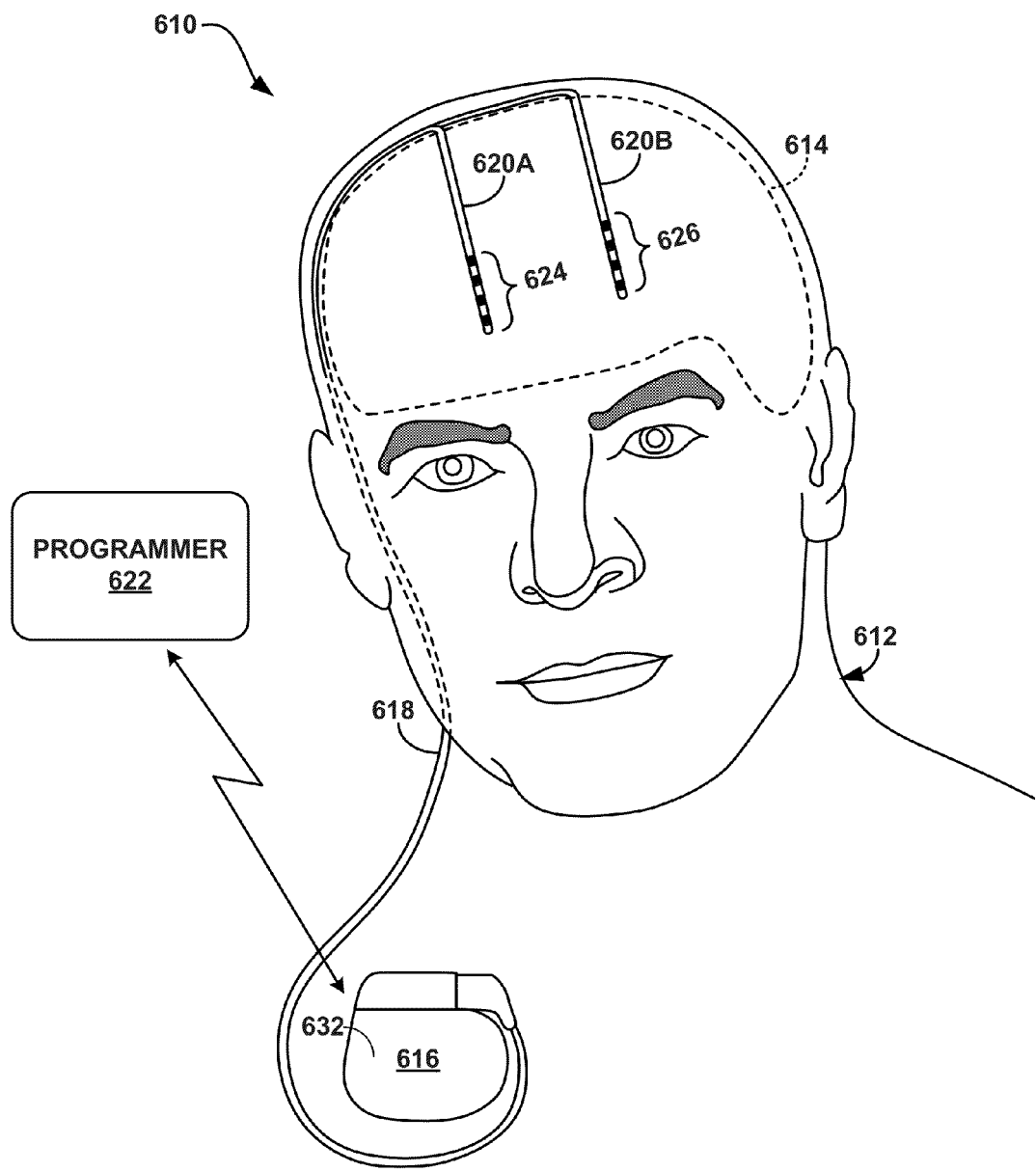
FIG. 6 is a conceptual diagram illustrating an example system that delivers therapy to a patient to manage a disorder of the patient.

FIG. 6 is a conceptual diagram illustrating an example therapy system 610 that monitors a brain condition and/or delivers therapy to patient 612 to manage the brain condition. System 610 includes implantable medical device (IMD) 616, lead extension 618, one or more leads 620A and 620B (collectively "leads 620") with respective sets of electrodes 624, 626 and medical device programmer 622. IMD 616 may include a module that includes monitoring circuitry that senses electrical brain signals and identifies brain activity and conditions via the electrodes 624, 626 of leads 620A and 620B, respectively.

System 610 may monitor one or more bioelectrical brain signals of patient 612. For example, IMD 616 may include a sensing module (e.g., sensing module 644 of FIG. 7) that senses bioelectrical brain signals within one or more regions of brain 614. In the embodiment shown in FIG. 6, the signals may be sensed by electrodes 624, 626 and conducted to the sensing module within IMD 616 via conductors within the respective lead 620A, 620B. As described in further detail below, in some embodiments, a processor of control circuitry of IMD 616 or another device (e.g., programmer 622) monitors the bioelectrical signals within brain 614 of patient 612 to detect a favorable brain state and/or performs the other functions referenced herein including those of FIGS. 1-5. A processor of control circuitry of IMD 616 or another device (e.g., programmer 622) may control delivery of electrical stimulation to brain 614 based on identification of a favorable brain state in a manner that treats a brain condition of patient 612.

In some examples, the sensing module of IMD 616 may receive the bioelectrical signals from electrodes 624, 626 or other electrodes positioned to monitor bioelectrical brain signals of patient 612 (e.g., if housing 632 of IMD 616 is implanted in or proximate brain 614, an electrode of housing 632 can be used to sense bioelectrical brain signals and/or deliver stimulation to brain 614). Electrodes 624, 626 may also be used to deliver electrical stimulation from stimulation generator 642 to target sites within brain 614 as well as to sense brain signals within brain 614. However, IMD 616 can also use separate sensing electrodes to sense the bioelectrical brain signals. In some embodiments, the sensing module of IMD 616 may sense bioelectrical brain signals via one or more of the electrodes 624, 626 that are also used to deliver electrical stimulation to brain 614. In other embodiments, one or more of electrodes 624, 626 may be used to sense bioelectrical brain signals while one or more different electrodes 624, 626 may be used to deliver electrical stimulation.

The bioelectrical brain signals monitored by IMD 616 may reflect changes in electrical current produced by the sum of electrical potential differences across tissue, such as brain tissue. Examples of the monitored bioelectrical signals include, but are not limited to, an EEG signal, an ECoG signal, a LFP signal sensed from within one or more regions of brain 614, and/or action potentials from single cells within the brain 614 of one or more networks. These and other signals can be used to perform the various functions referenced herein, including detection of a favorable brain state.

As discussed herein, the monitored brain signals of patient 612 may be used to monitor a favorable brain state of brain 614. Metrics that can be used to detect network activation and further characterize episodes of a favorable brain state include time domain characteristics (e.g., an amplitude or frequency) and/or frequency domain characteristics (e.g., an energy level as measured by power in one or more frequency bands) of the brain signals sensed by IMD 616 within one or more regions of brain 614. For example, the characteristic of the brain signals may include an absolute amplitude value or a root mean square amplitude value. In addition, the amplitude value may comprise an average, peak, mean or instantaneous amplitude value over a period of time or a maximum amplitude or an amplitude in a particular percentile of the maximum (e.g., an amplitude value that represents 95% of the maximum amplitude value).

As another example, the characteristic of the brain signal may include the frequency, amplitude, and phase of the bioelectrical brain signal(s) sensed within one or more regions of brain 614 of patient 612 associated with the different brain areas. The frequency, amplitude, and phase of the bioelectrical brain signal may indicate the oscillations in the brain signal and be used to identify or otherwise characterize a favorable brain state. The oscillations in the sensed bioelectrical brain signals may represent the rhythmic or repetitive neural activity in brain 614 when a particular network of an area is activated to perform a particular function. The neural oscillations may be determined based on one or more frequency domain characteristics of the bioelectrical brain signal.

As described in further detail below, IMD 616 may deliver therapy to any suitable portion of brain 614 that may play a role in affecting a favorable brain state in various embodiments. In some embodiments, system 610 may deliver therapy to patient 612 to manage a neurological disorder of patient 612. For example, system 610 may provide therapy to correct a brain disorder and/or manage symptoms of a neurodegenerative brain condition. Patient 612 ordinarily will be a human patient. In some cases, however, system 610 may be applied to other mammalian or non-mammalian non-human patients. While examples of the disclosure are described with regard to tracking and treatment of Parkinson's disease, in other examples, system 610 may track and/or provide therapy to manage symptoms of other patient conditions.

IMD 616 may include a module that includes a stimulation generator 642 that generates and delivers electrical stimulation therapy to one or more regions of brain 614 of patient 612 via the electrodes 624, 626 of leads 620A and 620B, respectively. In the example shown in FIG. 6, system 610 may be referred to as deep brain stimulation (DBS) system because IMD 616 may provide electrical stimulation therapy directly to tissue within brain 614, e.g., a tissue site under the dura mater of brain 614. In other embodiments, leads 620 may be positioned to sense brain activity and/or deliver therapy to a surface of brain 614, such as the cortical surface of brain 614, or other location in or along the patient 612.

In the example shown in FIG. 6, IMD 616 may be implanted within a subcutaneous pocket below the clavicle of patient 612. In other embodiments, IMD 616 may be implanted within other regions of patient 612, such as a subcutaneous pocket in the abdomen or buttocks of patient 612 or proximate the cranium of patient 612. Implanted lead extension 618 is coupled to IMD 616 via a connector block (also referred to as a header), which may include, for example, electrical contacts that electrically couple to respective electrical contacts on lead extension 618. The electrical contacts electrically couple the electrodes 624, 626 carried by leads 620 to IMD 616. Lead extension 618 traverses from the implant site of IMD 616 within a chest cavity of patient 612, along the neck of patient 612 and through the cranium of patient 612 to access brain 614. Generally, IMD 616 is constructed of a biocompatible material that resists corrosion and degradation from bodily fluids. IMD 616 may comprise a hermetic housing 632 to substantially enclose control circuitry and other components, such as a processor, sensing circuitry, therapy module, and memory. In some implementations, IMD 616 and other components (e.g., leads 620) may be implanted only in the head of the patient (e.g., under the scalp) and not in the chest and neck regions.

Electrical stimulation may be delivered to one or more regions of brain 614, which may be selected based on many factors, such as the type of patient condition for which system 610 is implemented to manage. In some cases, leads 620 may be implanted within the right and left hemispheres of brain 614 (e.g., as illustrated in FIG. 6) while, in other examples, one or both of leads 620 may be implanted within one of the right or left hemispheres. Other implant sites for leads 620 and IMD 616 are contemplated. For example, in some examples, IMD 616 may be implanted on or within cranium. In addition, in some examples, leads 620 may be coupled to a single lead that is implanted within one hemisphere of brain 614 or implanted through both right and left hemispheres of brain 614.

Leads 620 may be positioned to deliver electrical stimulation to one or more target tissue sites within brain 614 to manage patient symptoms associated with a disorder of patient 612. Targeted tissues may be the tissues identified as supporting a favorable brain state, such as identification of which area(s) of the brain 614 are activated when a patient is known to be in a favorable brain state. Leads 620 may be implanted to position electrodes 624, 626 at desired locations of brain 614 through respective holes in cranium. Leads 620 may be placed at any location within or along brain 614 such that electrodes 624, 626 are capable of providing electrical stimulation to target tissue sites of brain 614 during treatment. In some embodiments, leads may be placed such that electrodes 624, 626 directly contact or are otherwise proximate targeted tissue of a particular brain area.

In the example shown in FIG. 6, electrodes 624, 626 of leads 620 are shown as ring electrodes. Ring electrodes may be relatively easy to program and are typically capable of sensing and/or delivering an electrical field to any tissue adjacent to leads 620 (e.g., in all directions away from an outer perimeter of leads 620). In other examples, electrodes 624, 626 of leads 620 may have different configurations. For example, electrodes 624, 626 of leads 620 may have a complex electrode array geometry that is capable of producing shaped electrical fields. The complex electrode array geometry may include multiple electrodes (e.g., partial ring or segmented electrodes) around the perimeter of each lead 620, rather than a ring electrode. In this manner, electrical brain sensing and/or electrical stimulation may be associated with a specific direction from leads 620 (e.g., in a direction less than around the entire outer perimeter of leads 620) to enhance direction sensing and/or therapy efficacy and reduce possible adverse side effects from stimulating a large volume of tissue. As such, electrodes can be positioned to stimulate targeted tissue and avoid stimulating non-targeted tissue.

In some embodiments, outer housing 632 of IMD 616 may include one or more stimulation and/or sensing electrodes. For example, housing 632 can comprise an electrically conductive material that is exposed to tissue of patient 612 when IMD 616 is implanted in patient 612, or an electrode can be attached to housing 632. In alternative examples, leads 620 may have shapes other than elongated cylinders as shown in FIG. 6. For example, leads 620 may be paddle leads, spherical leads, bendable leads, or any other type of shape effective in treating patient 612.

In some examples, the location of the electrodes 624, 626 within brain 614 can be determined based on analysis of a bioelectrical brain signal of the patient sensed via one or more of the electrodes 624, 626. For example, a particular physiological structure (e.g., the amygdala) may exhibit a unique electrical signal and, thus, facilitate positioning of the electrodes of the lead at the desired implant location through monitoring of the bioelectrical brain signal.

Stimulation generator 642, under the control of processor 640, generates stimulation signals for delivery to patient 612 via selected combinations of electrodes 624, 626. Processor 640 controls stimulation generator 642 according to stimulation programs 652 stored in memory 641 to apply particular stimulation parameter values specified by one or more programs, such as amplitude, pulse width, timing, and pulse rate, in accordance with the various embodiments of this disclosure. In some embodiments, stimulation generator 642 generates and delivers stimulation signals to one or more target portions of brain 614 via a select combination of electrodes 624, 626

Leads 620 may be implanted within a desired location of brain 614 via any suitable technique, such as through respective burr holes in a skull of patient 612 or through a common burr hole in the cranium. Leads 620 may be placed at any location within brain 614 such that electrodes 624, 626 of leads 620 are capable of sensing electrical activity of the brain areas of (e.g., those associated with supporting a favorable brain state) and/or providing electrical stimulation to targeted tissue for treatment (e.g., to stimulate to facilitate potentiation of the favorable brain state).

In some examples, a processor of control circuitry of system 610 (e.g., a processor of programmer 622 or IMD 616) controls delivery of electrical stimulation by activating electrical stimulation, deactivating electrical stimulation, increasing the intensity of electrical stimulation, or decreasing the intensity of electrical stimulation delivered to brain 614 to titrate electrical stimulation therapy to facilitate potentiation of a favorable brain state. Therapy can be started, stopped, and/or changed by a processor in any manner and based on any parameter or finding as discussed herein.

System 610 may also store a plurality of stimulation programs (e.g., a set of electrical stimulation parameter values), and at least one stimulation program may be associated with at least one favorable brain state. A processor of IMD 616 or programmer 622 may select a stored stimulation program that defines electrical stimulation parameter values for delivery of electrical stimulation to brain 614 based on a characterization of a favorable brain state. Where IMD 616 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities.

External programmer 622 wirelessly communicates with IMD 616 as needed to provide or retrieve information. For example, external programmer 622 may receive sensed data and/or information regarding one or more episodes of a favorable brain state from IMD 616, as well as send therapy program information to IMD 616. Programmer 622 is an external computing device that the user, e.g., the clinician and/or patient 612, may use to communicate with IMD 616. For example, programmer 622 may be a clinician programmer that the clinician uses to communicate with IMD 616 and program one or more therapy programs for IMD 616. Additionally or alternatively, programmer 622 may be a patient programmer that allows patient 612 to input information (e.g., a self evaluated assessment regarding symptoms), select programs, and/or view and modify therapy parameters.

Programmer 622 may be a hand-held computing device with a display viewable by the user and an interface for providing input to programmer 622 (i.e., a user input mechanism). For example, programmer 622 may include a small display screen (e.g., a liquid crystal display (LCD) or a light emitting diode (LED) display) that presents information to the user. In addition, programmer 622 may include a touch screen display, keypad, buttons, a peripheral pointing device or another input mechanism that allows the user to navigate though the user interface of programmer 622 and provide input. If programmer 622 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 622 may be a touch screen that allows the user to provide input directly to the user interface shown on the display. The user may use a stylus or their finger to provide input to the display.

In various embodiments, programmer 622 may be a larger workstation or a separate application within another multi-function device, rather than a dedicated computing device. For example, the multi-function device may be a notebook computer, tablet computer, workstation, cellular phone, personal digital assistant or another computing device.

When programmer 622 is configured for use by the clinician, programmer 622 may be used to transmit initial programming information to IMD 616. This initial information may include hardware information, such as the type of leads 620, the arrangement of electrodes 624, 626 on leads 620, the position of leads 620 within brain 614, initial programs defining therapy parameter values, and any other information that may be useful for programming into IMD 616. Programmer 622 may also be capable of completing functional tests (e.g., measuring the impedance of electrodes 624, 626 of leads 620).

The clinician may also store therapy programs within IMD 616 with the aid of programmer 622. During a programming session, the clinician may determine one or more stimulation programs that may effectively bring about a therapeutic outcome that treats a brain condition, such as potentiating a favorable brain state. For example, the clinician may select one or more electrode combinations with which stimulation is delivered to brain 614 to potentiate a favorable brain state. During the programming session, the clinician may evaluate the efficacy of the one or more electrode combinations based on one or more findings of fMRI, patient self reporting, LFP, EEG, or some other parameters for characterizing episodes of a favorable brain state. In some examples, programmer 622 may assist the clinician in the creation/identification of stimulation programs by providing a methodical system for identifying potentially effective stimulation parameter values, such as by having a predetermined index of types of favorable brain states and stimulation parameters predetermined to be particularly effective in potentiating the respective types of favorable brain states. In some examples, the processor of control circuitry of programmer 622 may calculate and display one or more therapy metrics for evaluating and comparing therapy programs available for delivery of therapy from IMD 616 to patient.

Programmer 622 may also provide an indication to patient 612 when therapy is being delivered which may aid the assessment of therapy efficacy. For example, following the delivery of electrical stimulation for multiples episodes of detection of a favorable brain state, the patient may evaluate whether he or she seems to have decreased symptoms by answering questions presented on the programmer 622, which can be used in evaluating potentiation of a favorable brain state and titrating therapy.

Whether programmer 622 is configured for clinician or patient use, programmer 622 is configured to communicate with IMD 616 and, optionally, another computing device, via wireless communication. Programmer 622, for example, may communicate via wireless communication with IMD 616 using radio frequency (RF) telemetry techniques known in the art. Programmer 622 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 622 may also communicate with other programming or computing devices via exchange of removable media, such as magnetic or optical disks, memory cards or memory sticks. Further, programmer 622 may communicate with IMD 616 and another programmer via remote telemetry techniques known in the art, communicating via a local area network (LAN), wide area network (WAN), public switched telephone network (PSTN), or cellular telephone network, for example.

Figure 7:
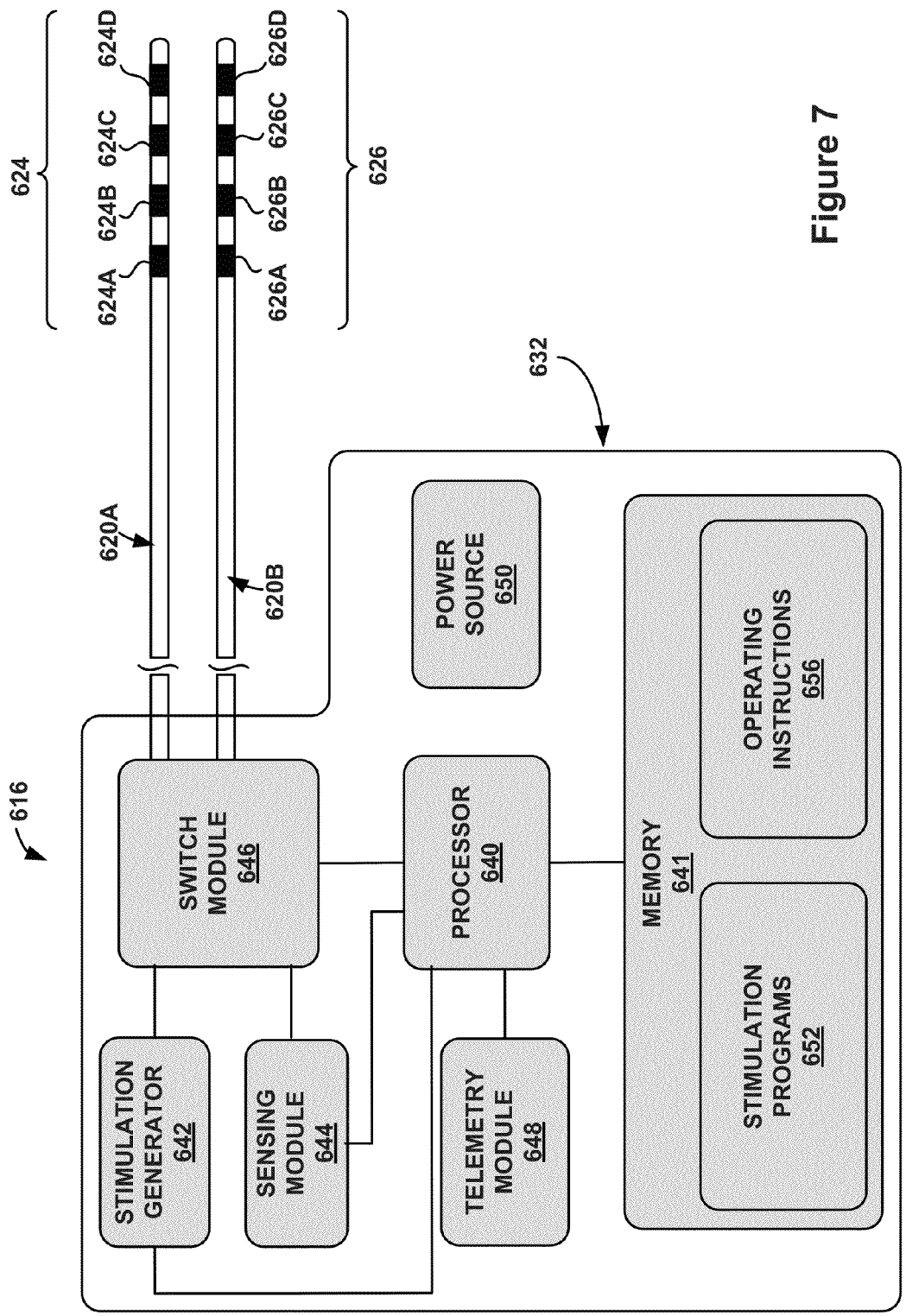
FIG. 7 is a functional block diagram illustrating control circuitry of an implantable medical device.

FIG. 7 is a functional block diagram illustrating components of IMD 616. In the configuration shown in FIG. 7, IMD 616 includes control circuitry components including processor 640, memory 641, stimulation generator 642, sensing module 644, switch module 646, telemetry module 648, and power source 650. Memory 641 may include any volatile or non-volatile media, such as a random access memory (RAM), read only memory (ROM), non-volatile RAM (NVRAM), electrically erasable programmable ROM (EEPROM), flash memory, and the like. Memory 641 may store computer-readable instructions that, when executed by processor 640, cause IMD 616 to perform various functions described herein. Memory 641 may include operating instructions 656 executable by the processor 640 for causing the IMD 616 to carry out the functions referenced herein, including those discussed in association with FIGS. 1-5. Memory 641 may store therapy instructions as part of stimulation programs 652 that are available to be selected by processor 640 in response to detection of a favorable brain state from the sensing module 644. In addition, processor 640 may be configured to record diagnostic information, such as sensed signals, signal characteristics, brain state episode information, or the like in memory 641 or another memory or storage device. The various functions and options described herein may be performable automatically by the IMD 616 by processor 640 execution of operating instructions 656 and stimulation programs 652 stored in memory 641.

The steps, procedures, techniques, etc. referenced herein may be carried out in part by, for example, software instructions, such as those used to define a software or computer program. The computer-readable medium (e.g., memory 641) may store instructions (e.g., operating instructions 656 and stimulation programs 652) executable to carry out the steps, procedures, techniques, etc. In this way, control circuitry, having a processor and memory, can be configured to perform the various steps, procedures, techniques, etc. as described herein, including those discussed in association with FIGS. 1-5. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a processor to perform the actions described herein.

Processor 640 may determine whether a sensed bioelectrical brain signal includes a biomarker (e.g., a particular power level of a particular frequency band) indicative of a favorable brain state. Processor 640 may analyze a sensed bioelectrical signal for correlation with a template, or a specific stored value. For example, the peak, lowest, or average amplitude of the bioelectrical brain signal (or other characteristic of a bioelectrical signal) may be compared to a threshold, the crossing of the threshold indicating presence of the favorable brain state.

As another technique that can be implemented by a processor for detection of a favorable brain state, memory 641 may store portions of bioelectrical brain signals (e.g., waveforms or specific values of signal characteristics) previously sensed within brain 614 of patient 612 (or based on clinical data) that correspond to a favorable brain state that is confirmed by MRI and/or symptom relief. In some examples, the stored bioelectrical brain signals can be used as a template to determine whether a particular sensed bioelectrical brain signal is indicative of the favorable brain state. As an example of a signal processing technique that processor 640 may employ to determine whether the bioelectrical brain signal includes the biomarker associated with a favorable brain state, processor 640 may analyze the bioelectrical brain signal with feature correlation, temporal correlation, or frequency correlation with a template signal, or combinations thereof. As another example, a slope of the amplitude of the bioelectrical brain signal over time or timing between inflection points or other critical points in the pattern of the amplitude of the bioelectrical brain signal over time may be compared to trend information stored in memory. A correlation between the inflection points in the amplitude waveform of the bioelectrical brain signal or other critical points and a template may indicate the bioelectrical brain signal includes the biomarker indicative of the a favorable brain state, which may be validated by comparison to MRI images showing activation of one or more brain areas in support of the favorable brain state and/or confirmation from the patient or sensors that symptoms are decreased.

As another technique for detection of a favorable brain state, processor 640 as part of control circuitry may perform temporal correlation by sampling the waveform generated by a sensed bioelectrical brain signal with a sliding window and comparing the waveform with a template waveform stored in memory that is associated with the favorable brain state. For example, processor 640 may perform a correlation analysis by moving a window along a digitized plot of the amplitude waveform of a sensed bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform and the waveform of the plot of the sensed bioelectrical brain signal over time, or by applying any suitable mathematical correlation algorithm between the sample in the sampling window and a corresponding set of samples stored in the template waveform. The template may be validated by comparison to MRI images and/or confirmation from the patient or sensors that symptoms are decreased.

Processor, as used herein, such as processor 640, may include any of one or more of a microprocessor, a controller, a digital signal processor (DSP), an application specific integrated circuit (ASIC), one or more gate arrays (e.g., a field-programmable gate array (FPGA)), discrete logic circuitry, and any number of each. The functions attributed to the control circuitry and/or a processor may be embodied as firmware, hardware, software or any combination thereof specifically configured (e.g., with programming) to carry out those functions.

For example, processor 640, as part of control circuitry, may by configured to control stimulation generator 642 to deliver electrical stimulation with pulse voltage or current amplitudes, pulse widths, and frequencies (i.e., pulse rates), and electrode combinations specified by the stimulation programs 652 with predetermined delays, e.g., as stored in memory 641. Processor 640, as part of control circuitry, may control stimulation generator 642 to deliver each pulse, or a burst of pulses, according to a different program of the stimulation programs, such that multiple programs of stimulation are delivered on an interleaved or alternating basis, e.g., having different delays or responding to different brain states, based on the detection of respective favorable brain states that are different. In some embodiments, processor 640 may control stimulation generator 642 to deliver a substantially continuous stimulation waveform rather than pulsed stimulation.

As shown, the set of electrodes 624 of lead 620A includes electrodes 624A, 624B, 624C, and 624D, and the set of electrodes 626 of lead 620B includes electrodes 626A, 626B, 626C, and 626D. Processor 640 may control switch module 646 to apply the stimulation signals generated by stimulation generator 642 to selected combinations of electrodes 624, 626. In particular, switch module 646 may couple stimulation signals to selected conductors within leads 620, which, in turn, deliver the stimulation signals across selected electrodes 624, 626. Switch module 646 may be a switch array, switch matrix, multiplexer, or any other type of switching module configured to selectively couple stimulation energy to selected electrodes 624, 626 and to selectively sense bioelectrical brain signals with selected electrodes 624, 626. Hence, stimulation generator 642 is coupled to electrodes 624, 626 via switch module 646 and conductors within leads 620. In some embodiments, however, IMD 616 does not include switch module 646.

Sensing module 644 is configured to sense bioelectrical brain signals of patient 612 via a selected subset of electrodes 624, 626, or with one or more electrodes 624, 626 and at least a portion of a conductive outer housing 632 of IMD 616, an electrode on an outer housing of IMD 616, or another reference. Processor 640 may control switch module 646 to electrically connect sensing module 644 to selected electrodes 624, 626. In this way, sensing module 644 may selectively sense bioelectrical brain signals with different combinations of electrodes 624, 626 (and/or a reference other than an electrode 624, 626). Although bioelectrical brain signals are used as an exemplar herein, or sensed signals are also contemplated, including signals that could indicate a favorable brain state. Although the electrodes 624, 626 are principally described as being implanted within a brain in the manner of DBS, other locations are additionally or alternatively contemplated. For example, electrodes may be deployed at selected tissue sites or on selected surfaces of a human patient, such as on the brain, along the cortex, proximate the spinal cord, on the scalp, or elsewhere. As an example, scalp electrodes may be used to measure or record EEG signals. As another example, electrodes implanted at the surface of the cortex may be used to measure or record ECoG signals. In some embodiments, an external device may be worn with sensing elements positioned at a desired location adjacent the patient to detect a physiological signal (e.g., a brain signal).

Sensing module 644 may form part of a sensor circuit configured to monitor a variety of signals via a variety of different sensing elements, such as a brain signals via electrodes 624, 626, and/or other physiological signals. Sensing module 644 and/or processor 640 (and/or other circuitry) may monitor the signals to identify a favorable brain state or performed the other monitoring techniques referenced herein. In some embodiments, sensing module 644 may directly process signals obtained from electrodes 624, 626 or other sensing elements with little or no preprocessing by other components. In other embodiments, sensing module 644 may include preprocessing circuitry to process or convert signals for analysis by processor 640 or other circuitry. In some embodiments, sensing module 644 includes circuitry configured to measure one or more parameters of an electrical signal, such as amplitude, and processor 640 receives an output from the telemetry module 648 of an indication of the measurement for further analysis as discussed herein, such as determining whether the measurement exceeds a threshold.

Clinician, processor 640 of IMD 616, and/or a processor of another device, such as programmer 622, may determine the one or more biomarkers indicative of a favorable brain state based on the bioelectrical brain signal(s). The biomarkers may be selected by the clinician or automatically by a processor, and may be selected as the signal characteristics that distinguish the bioelectrical brain signal sensed during occurrence of a favorable brain state from a bioelectrical brain signal sensed at other times without such occurrence of the favorable brain state, which may be distinguished based on the whether the patient is experiencing symptoms relief temporally correlated with the bioelectrical brain signal. The biomarker can then serve as a favorable brain state threshold or other indicator for subsequent detection of a favorable brain state.

Processor 640 or other part of control circuitry may monitor bioelectrical brain signals sensed by sensing module 644 in any suitable manner in order to detect and characterize a favorable brain state and the absence of the favorable brain state. For example, sensing module 644 may directly sense one or more bioelectrical brain signals, e.g., a LFP, via one or more of electrodes 624, 626 at a particular point within a portion of brain 614 that supports a favorable brain state, and processor 640 may monitor the bioelectrical brain signal. Memory 641 may store information related to threshold values for signal characteristics that demarcate a favorable brain state, and processor 640 may compare characteristics of the sensed bioelectrical brain signals to the stored threshold values to detect a favorable brain state. Processor 640 or other part of control circuitry may further characterize the favorable brain state by, for example, determining the phase or period of the signal that indicates the favorable brain state.

In various embodiments, system 610 may include one or more external electrodes positioned on the outer surface of the cranium of patient 612 that can sense and generate a bioelectrical brain signal that can be used to detect and characterize a favorable brain state. Such detection and characterization of a favorable brain state may use the techniques discussed herein for detecting and characterizing a favorable brain state via internally sensed signals (e.g., comparing signals, frequency or other parameter match, a biomarker, template, and/or other technique).

Although sensing module 644 is incorporated into a common housing 632 with stimulation generator 642 and processor 640, in other examples, sensing module 644 is in a physically separate outer housing from outer housing 632 of IMD 616 and communicates with processor 640 via wired or wireless communication techniques.

Telemetry module 648 supports wireless communication between IMD 616 and an external programmer 622 or another computing device under the control of processor 640. Processor 640 of IMD 616 may receive, as updates to sensing and/or stimulation programs, values for stimulation parameters such as amplitude and electrode combination information from programmer 622 via telemetry module 648. The updates to the stimulation, sensing, or other programs may be stored within stimulation programs 652 of memory 641. Telemetry module 648 in IMD 616, as well as telemetry modules in other devices and systems described herein, such as programmer 622, may accomplish communication by RF communication or inductance techniques, among other transcutaneous communication techniques. For example, telemetry module 648 may communicate with external medical device programmer 622 via proximal inductive interaction of IMD 616 with programmer 622. Accordingly, telemetry module 648 may send information to external programmer 622 on a continuous basis, at periodic intervals, or upon request from IMD 616 or programmer 622. For example, processor 640 may transmit sensed signals and/or network activation information to programmer 622 via telemetry module 648.

Power source 650 delivers operating power to various components of IMD 616. Power source 650 may include a small rechargeable or non-rechargeable battery and a power generation circuit to produce the operating power. Recharging may be accomplished through proximal inductive interaction between an external charger and an inductive charging coil within IMD 616. In some examples, power requirements may be small enough to allow IMD 616 to utilize patient motion and implement a kinetic energy-scavenging device to trickle charge a rechargeable battery. In various embodiments, traditional batteries may be used.

The techniques described in this disclosure, including the steps of FIGS. 1-5 and those attributed to programmer 622, IMD 616, control circuitry, a processor, or various constituent components, may be implemented, at least in part, in hardware, software, firmware or any combination thereof as control circuitry. For example, the IMD 616 may have control circuitry as shown in FIG. 7 for automatically carrying out the techniques discussed herein, including the methods of FIGS. 1-5. Such hardware, software, firmware may be implemented as control circuitry within the same device or within separate devices to support the various operations and functions described in this disclosure. While the techniques described herein are primarily described as being performed by control circuitry, processor 640 of IMD 616 and/or processor of a programmer or other external device, any of the one or more parts of the techniques described herein may be implemented by control circuitry of one of IMD 616, programmer 622, or another computing device, alone or in combination with each other. For example, the various functional options discussed in connection with FIGS. 1-5 can be implemented by a processor executing program instructions stored in memory as part of control circuitry configured to perform the various described functions, including the method steps.

A processor, as used herein, refers to any number and/or combination of a microprocessor, a digital signal processor (DSP), an application specific integrated circuit (ASIC), a field-programmable gate array (FPGA), microcontroller, discrete logic circuitry, processing chip, gate arrays, and/or any other equivalent integrated or discrete logic circuitry. "Control circuitry" as used herein refers to at least one of the foregoing logic circuitry as a processor, alone or in combination with other circuitry, such as memory or other physical medium for storing instructions, as needed to carry about specified functions (e.g., a processor and memory having stored program instructions executable by the processor for analyzing a signal sensed via a sensing module to identify one or more episodes of a favorable brain state and deliver stimulation based on the identification). The functions referenced herein and those functions of FIGS. 1-5, may be embodied as firmware, hardware, software or any combination thereof as part of control circuitry specifically configured (e.g., with programming) to carry out those functions, such as in means for performing the functions referenced herein. The steps described herein may be performed by a single processing component or multiple processing components, the latter of which may be distributed amongst different coordinating devices (e.g., an IMD and an external programmer). In this way, control circuitry may be distributed between multiple devices, including an implantable medical device and an external medical device in various systems. In addition, any of the described units, modules, or components may be implemented together or separately as discrete but interoperable logic devices of control circuitry. Depiction of different features as modules or units is intended to highlight different functional aspects and does not necessarily imply that such modules or units must be realized by separate hardware or software components and/or by a single device. Rather, functionality associated with one or more module or units, as part of control circuitry, may be performed by separate hardware or software components, or integrated within common or separate hardware or software components of the control circuitry.

When implemented in software, the functionality ascribed to the systems, devices and control circuitry described in this disclosure may be embodied as instructions on a physically embodied computer-readable medium such as RAM, ROM, NVRAM, EEPROM, FLASH memory, magnetic data storage media, optical data storage media, or the like, the medium being physically embodied in that it is not a carrier wave, as part of control circuitry. The instructions may be executed to support one or more aspects of the functionality described in this disclosure.

While Parkinson's disease is generally used as an exemplar for describing various aspects of the present disclosure, it is contemplated that the techniques and devices could be applied to other neural conditions, such as cognitive impairment, spinal injury, and traumatic brain damage, among others. Furthermore, it is contemplated that various brain conditions may be characterized by the loss of connection and function of one or more brain networks. Various embodiments can concern monitoring signals and delivering electrical stimulation in response to detection of a particular brain state to potentiate the particular brain state. Such embodiments may further include titrating one or more parameters of the electrical stimulation to increase frequency, strength, and/or duration of the particular brain state. One having ordinarily skill in the art will appreciate that the various techniques, options, features, and components discussed herein are applicable to such embodiments, such as in implementation by an IMD or other device having appropriately configured circuitry.

Various examples have been described. These and other examples are within the scope of the following claims.

We claim:

1. A method of treating a patient with a brain condition, comprising:

monitoring, via a sensor, a signal of the brain of the patient;

detecting, based on the brain signal, a brain state of the patient, the brain state of the patient being indicative of one or more areas of the brain being activated when the patient is experiencing the brain state; and delivering, via a therapy module, electrical stimulation that potentiates the brain state by targeting one or more of the activated areas of the brain, the electrical stimulation being delivered only within a window of time that opens in response to detection of the brain state, the window of time extending no greater than 250 milliseconds from occurrence of the brain state.

2. The method of claim 1, wherein detecting the brain state comprises identifying the brain state from among multiple predetermined brain states associated with the brain condition.

3. The method of claim 2, wherein the brain state is identified by comparing a pattern of the brain signal to patterns respectively associated with each of the multiple predetermined brain states associated with the brain condition.

4. The method of claim 1, further comprising:
determining the patient is in a brain state associated with reduced symptoms of the brain condition; and
storing a pattern of the brain signal monitored while the patient is in the brain state associated with reduced symptoms of the brain condition as one of the multiple predetermined brain states.

5. The method of claim 4, wherein determining the patient is in a brain state associated with reduced symptoms of the brain condition comprises receiving input from the patient.

6. The method of claim 1, wherein the brain state is associated with a decrease in one or more symptoms of the brain condition.

7. The method of claim 1, wherein detecting the brain state comprises recognizing one or more patterns in one or more brain signals that correspond to one or more stored biomarkers of the brain state.

8. The method of claim 1, wherein detecting the brain state comprises detecting a power level of a frequency band of the brain signal crossing a threshold.

9. The method of claim 1, wherein detecting the brain state comprises detecting the brain transitioning from one brain state to a different brain state.

10. The method of claim 1, further comprising titrating one or more delivery parameters of the electrical stimulation to increase the potentiation effect of the electrical stimulation on the brain state.

11. The method of claim 1, further comprising titrating one or more delivery parameters of the electrical stimulation based on increasing one or both of frequency and duration of occurrence of the brain state.

12. The method of claim 1, further comprising titrating one or more delivery parameters of the electrical stimulation based on increasing an amplitude of the brain signal.

13. The method of claim 1, further comprising:
identifying one or more brain signal biomarkers of the patient as indicative of the brain state; and
storing the one or more brain signal biomarkers in memory, wherein detecting the brain state comprises recognizing presence of at least one of the biomarkers in the brain signal.

14. The method of claim 1, wherein the electrical stimulation comprises only one or two pulses delivered within the window of time which is opened for each detection of occurrence of the brain state.

15. The method of claim 1, wherein delivery of the electrical stimulation is timed to coincide with a particular phase of the brain signal that indicates the brain state.

16. The method of claim 1, wherein:
detecting the brain state comprises detecting a plurality of brain state events; and
delivering the electrical stimulation comprises delivering one or more pulses to the brain for each of the plurality of detected brain state events.

17. The method of claim 1, wherein the window of time spans from the beginning of occurrence of the brain state and extends no greater than 100 milliseconds from the end of occurrence of the brain state.

18. The method of claim 1, wherein the brain signal comprises one or more local field potential signals sensed from implanted electrodes.

19. A system comprising:
a sensor configured to receive a signal indicative of a brain state of a patient;
a stimulation generator configured to generate electrical stimulation; and
control circuitry configured to detect the brain state based on the signal, the brain state of the patient being indicative of one or more areas of the brain being activated when the patient is experiencing the brain state, and control delivery of the electrical stimulation to potentiate the brain state by targeting one or more of the activated areas of the brain, the electrical stimulation being delivered only within a window of time that opens in response to detection of the brain state, the window of time extending no greater than 250 milliseconds from occurrence of the brain state.

20. The system of claim 19, wherein the brain signal comprises one or more brain signals, and wherein the control circuitry is configured to detect the brain state by recognizing one or more patterns in the one or more brain signals that correspond to one or more biomarkers indicative of the brain state.

21. The system of claim 19, wherein the control circuitry is configured to detect the brain state based on a power level of a frequency band of the brain signal crossing a threshold.

22. The system of claim 19, wherein the control circuitry is configured to detect the brain state based on the brain state transitioning from one brain state to a different brain state.

23. The system of claim 19, wherein the control circuitry is configured to titrate one or more delivery parameters of the electrical stimulation based on increasing the potentiation effect of the electrical stimulation on the brain state.

24. The system of claim 19, wherein the control circuitry is configured to titrate one or more delivery parameters of the electrical stimulation based on increasing one or both of frequency and duration of occurrence of the brain state.

25. The system of claim 19, wherein the control circuitry is configured to titrate one or more delivery parameters of the electrical stimulation based on increasing the amplitude of the brain signal.

26. The system of claim 19, wherein the control circuitry is configured to identify one or more brain signal biomarkers of the patient as indicative of the brain state and store the one or more brain signal biomarkers in memory, wherein the control circuitry is configured to detect the brain state by recognizing presence of the one or more biomarkers in the one or more brain signals.

27. The system of claim 26, wherein the control circuitry is configured to identify the one or more brain signal biomarkers of the patient based on input from the patient.

28. The system of claim 27, wherein the input from the patient is input that indicates an improvement of a brain condition of the patient associated with the brain state.

29. The system of claim 19, wherein the electrical stimulation comprises only one or two pulses delivered within the window of time which is opened for each detection of the brain state.

30. The system of claim 19, wherein the control circuitry is configured to time delivery of the electrical stimulation to coincide with a particular phase of the brain signal.

31. The system of claim 19, wherein the window of time spans from the beginning of occurrence of the brain state and extends no greater than 100 milliseconds from the end of occurrence of the brain state.

32. The system of claim 19, wherein the sensor comprises an implantable brain electrode and the brain signal comprise one or more local field potential signals.

33. The system of claim 19, wherein the control circuitry is configured to detect the brain state by identifying the brain state from among multiple predetermined brain states associated with a brain condition of the patient.

34. The system of claim 33, wherein control circuitry is configured to detect the brain state by comparing a pattern of the brain signal to patterns respectively associated with each of the multiple predetermined brain states associated with the brain condition.

35. A system, comprising:
means for monitoring a brain signal from the brain of a patient;
means for detecting a brain state based on the brain signal, the brain state of the patient being indicative of one or more areas of the brain being activated when the patient is experiencing the brain state; and
means for delivering electrical stimulation that potentiates the brain state by targeting one or more of the activated areas of the brain, the electrical stimulation being delivered only within a window of time that opens in response to detection of the brain state, the window of time extending no greater than 250 milliseconds from occurrence of the brain state.

36. A physically embodied computer-readable medium comprising instructions that cause a processor to:
monitor a brain signal;
detect a brain state based on the brain signal, the brain state being indicative of one or more areas of the brain being activated when a patient is experiencing the brain state; and
deliver electrical stimulation to potentiate the brain state by targeting one or more of the activated areas of the brain, the electrical stimulation being delivered only within a window of time that opens in response to detection of the brain state and that extends no greater than 250 milliseconds from occurrence of the brain state.

37. The method of claim 1,
wherein monitoring, via the sensor, the signal of the brain of the patient includes monitoring the signal of the brain of the patient via electrodes implanted within the brain of the patient, and
wherein delivering, via the therapy module, the electrical stimulation that potentiates the brain state includes delivering the electrical stimulation that potentiates the brain state via the same electrodes implanted within the brain of the patient used for monitoring the signal of the brain of the patient.

38. The method of claim 1, wherein delivering the electrical stimulation that potentiates the brain state by targeting one or more of the activated areas of the brain includes treating the targeted activated areas of the brain remotely by delivering the electrical stimulation to an associated brain area.

39. The method of claim 1, wherein delivering the electrical stimulation that potentiates the brain state by targeting one or more of the activated areas of the brain includes delivering the electrical stimulation to reinforce brain signals within the activated areas of the brain.

* * * * *